(12) United States Patent
Oda

(10) Patent No.: US 8,030,083 B2
(45) Date of Patent: Oct. 4, 2011

(54) METHOD OF ANALYZING PROTEIN STRUCTURAL AFFINITY RELATIONSHIP

(75) Inventor: Yoshiya Oda, Tsukuba (JP)

(73) Assignee: Eisai R & D Management Co., Ltd., Tokyo (JP)

(*) Notice: Subject to any disclaimer, the term of this patent is extended or adjusted under 35 U.S.C. 154(b) by 866 days.

(21) Appl. No.: 11/571,337

(22) PCT Filed: Jul. 4, 2005

(86) PCT No.: PCT/JP2005/012713
§ 371 (c)(1), (2), (4) Date: Dec. 27, 2006

(87) PCT Pub. No.: WO2006/004213
PCT Pub. Date: Jan. 12, 2006

(65) Prior Publication Data
US 2008/0057592 A1   Mar. 6, 2008

Related U.S. Application Data

(60) Provisional application No. 60/585,362, filed on Jul. 2, 2004.

(30) Foreign Application Priority Data

Nov. 17, 2004 (JP) ................................. 2004-333065

(51) Int. Cl.
G01N 33/00 (2006.01)
(52) U.S. Cl. ......................................... 436/86; 436/173
(58) Field of Classification Search ..................... 436/86
See application file for complete search history.

(56) References Cited

FOREIGN PATENT DOCUMENTS

| EP | 1 686 372 A1 | 8/2006 |
|---|---|---|
| JP | 2003-177131 A | 6/2003 |
| WO | WO 02/48716 | 6/2002 |

OTHER PUBLICATIONS

Aebersold et al. ("Mass spectrometry-based proteomics," Nature 2003, 422, 198-207).*
Griffith et al. ("Methionine aminopeptidase (type 2) is a common target for angiogenesis inhibitors AGM-1470 and ovalicin," Chemistry & Biology 1997, 4, 461-471).*

(Continued)

*Primary Examiner* — Yelena G Gakh
*Assistant Examiner* — Michelle Adams
(74) *Attorney, Agent, or Firm* — Dickstein Shapiro LLP

(57) ABSTRACT

A method for analyzing a structural affinity relationship between plural kinds of proteins and a compound, comprising the steps of (a) using a compound-immobilized carrier to purify plural kinds of proteins bound to the compound on the carrier, from a group of isotope-labeled proteins; (b) using a compound-immobilized carrier to purify plural kinds of proteins bound to the compound on the carrier, from a group of proteins brought into contact with a compound beforehand; (c) mixing the proteins obtained in step (a) and step (b); (d) analyzing the mixture obtained in step (c) with mass spectrometry; (e) identifying each of plural kinds of proteins based on information obtained by the mass spectrometry; and (f) obtaining an intensity ratio between a labeled peak and a non-labeled peak of each protein, thereby quantitating an affinity ratio of the compound to each protein.

13 Claims, 10 Drawing Sheets

OTHER PUBLICATIONS

Kudo et al. ("Leptomycin B inactivates CRM1/exportin 1 by covalent modification at a cysteine residue in the central conserved region," Proc. Natl. Acad. Sci. USA 1999, 96, 9112-9117).*

Sechi et al. ("Quantitative proteomics using mass spectroscopy," Current Opinion in Chemical Biology 2003, 7, 70-77, available Feb. 2003).*

Oda et al. ("Quantitative Chemical Proteomics for Identifying Candidate Drug Targets," Anal. Chem. 2003, 75, 2159-2165, available Apr. 3, 2003).*

Graves et al. ("Discovery of Novel Targets of Quinoline Drugs in the Human Purine Binding Proteome," Molecular Pharmacology 2002, 62,1364-1372.).*

Aebersold ("Constellations in a cellular universe," Nature 2003, 422, 115-116).*

Szardenings et al. ("Fishing for targets: novel approaches using small molecule baits," Drug Discovery Today, 2004, 1, 9-15, available Sep. 2004).*

Taunton et al. ("A Mammalian Histone Deacetylase Related to the Yeast Transcriptional Regulator Rpd3p," Science 1996, 272, 408-411).*

Sin et al. ("The anti-angiogenic agent fumagillin covalently binds and inhibits the methionine aminopeptidase, MetAp-2," Proc. Natl. Acad. Sci., USA 1997, 94, 6099-6103).*

Sin et al. ("Eponemycin Analogues: Syntheses and use as Probes of Angiogenesis," Bioorg. Med. Chem. 1998, 6, 1209-1217).*

Philip L. Ross, et al.; "Multiplexed Protein Quantitation in *Saccharomyces cerevisiae* Using Amine-reactive Isobaric Tagging Reagents"; Molecular & Cellular Proteomics 3.12, pp. 1154-1169, ©2004 by the American Society for Biochemistry and Molecular Biology, Inc.

Edited by Hiroshi Terada, Hirokawa, "Kagaku to Seibutsu Jikken Line 48 Tanpakushitsu to Kakusan no Bunri Siesei—Kiso to Jikken -", 2001, 13.2.4 Defferential display-ho, at p. 457.

Supervised by Shigeo Oono, Yoshifumi Nisimura, "Saibo Kogaku Bessatsu Jikken Protocol Series Tanpakushitsu Jikken Protocol Kino Kaisekihen", 1997, pp. 157 to 161.

Schulze W., et al.: "A Novel Proteomic Screen for Peptide-Protein Interaction"; The Journal of Biological Chemistry, vol. 279, No. 11, Issue of Mar. 12, 2004, pp. 10756-10764.

Blagoev, B., et al.;"A proteomics strategy to elucidate functional protein-protein interactions applied to EGF signaling"; Technical Report of Nature Biotechnology, Mar. 2003, vol. 21, pp. 315-318.

Burdine, L., et al.; "Target Identification in Chemical Genetics: The (Often) Missing Link"; Chemistry & Biology, vol. 11, May 2004, pp. 593-597.

Supplementary European Search Report issued for EP 0575 8170, dated Jan. 27, 2010.

Matthew W. Harding, et al.; "A receptor for the immunosuppressant FK506 is a *cis-trans* peptidyl-prolyl isomerase"; Nature, vol. 341, Oct. 26, 1989, pp. 758-760.

Noriaki Shimizu et al.; "High-performance affinity beads for identifying drug receptors"; Nature Biotechnology, vol. 18, Aug. 2000, pp. 877-881.

Eric C Griffith, et al.; "Methionine aminopeptidase (type 2) is the common target for angiogenesis inhibitors AGM-1470 and ovalicin"; Chemistry & Biology, 1997, vol. 4, No. 6, pp. 461-471.

M. Knockaert, et al.; "Intracellular targets of cyclin-dependent kinase inhibitors: identification by affinity chromatography using immobilised inhibitors"; Chemistry & Biology 2000, vol. 7, No. 6, pp. 411-422.

M. Knockaert, et al.; "Intracellular Targets of Paullones"; The Journal of Biological Chemistry, vol. 277, No. 28, Issue of Jul. 12, 2002, pp. 25493-25501.

Joachim B. Schnier, et al.; "Identification of cytosolic aldehyde dehydrogenase 1 from non-small cell lung carcinomas as a flavopiridol-binding protein"; FEBS Letters 454, 1999, pp. 100-104.

Astrid Kaiser, et al.; "The Cyclin-Dependent Kinase (CDK) Inhibitor Flavopiridol Inhibits Glycogen Phosphorylase"; Archives of Biochemistry and Biophysics, vol. 386, No. 2, Feb. 15, 2001, pp. 179-187.

Klaus Godl, et al.; "An efficient proteomics method to identify the cellular targets of protein kinase inhibitors"; PNAS, vol. 100, No. 26, Dec. 23, 2003; pp. 15434-15439.

Takashi Owa, et al.; "Discovery of Novel Antitumor Sulfonamides Targeting G1 Phase of the Cell Cycle"; Journal of Medical Chemistry, 1999, vol. 42, No. 19, pp. 3789-3799.

Steven P. Gygi, et al.; "Quantitative analysis of complex protein mixtures using isotope-coded affinity tags"; Nature Biotechnology, vol. 17, Oct. 1999, pp. 994-999.

David K Han, et al.; "Quantitative profiling of differentiation-induced microsomal proteins using isotope-coded affinity tags and mass spectrometry"; Nature Biotechnology, vol. 19, Oct. 2001, pp. 946-951.

Robert Tonge, et al.; "Validation and development of fluorescence two-dimensional differential gel electrophoresis proteomics technology"; Proteomics 2001, vol. 1, pp. 377-396.

Yoshiya Oda et al.; "Quantitative Chemical Proteomics for Identifying Candidate Drug Targets"; Analytical Chemistry, vol. 75, No. 9, May 1, 2003; pp. 2159-2165.

* cited by examiner

FIG.5

| Protein | Formulae | | | | |
|---|---|---|---|---|---|
| | 2 | 3 | 4 | 6 | 5 |
| chromosome 14 open reading frame 166 | 0.68 | 1.03 | 8.65 | 3.45 | 2.70 |
| guanine nucleotide binding protein (G protein), alpha inhibiting activity polypeptide 1 | 0.39 | 0.78 | 1.32 | 0.97 | 0.33 |
| arsA arsenite transporter, ATP-binding, homolog 1 | 1.94 | 2.99 | 6.79 | 1.67 | 3.18 |
| RAN binding protein 6 | 2.66 | 8.81 | 2.16 | 5.26 | 3.45 |
| ribosomal protein L11 | 2.63 | 4.76 | 3.21 | 3.23 | 6.79 |
| tubulin, beta polypeptide 4, member Q | 1.25 | 0.91 | 0.42 | 3.09 | 4.13 |
| beta 5-tubulin | 1.11 | 1.38 | 1.75 | 1.82 | 2.53 |
| glutathione-S-transferase omega 1 | 0.36 | 0.23 | 0.16 | 1.61 | 0.45 |
| beta tubulin 1, class VI | 1.25 | 1.02 | 1.61 | 3.03 | 2.68 |
| adaptor-related protein complex 2, alpha 2 subunit | 3.01 | 4.06 | 2.29 | 8.76 | 3.93 |
| importin 9 | 2.95 | 5.69 | 4.00 | 4.52 | 4.44 |
| tubulin, beta polypeptide paralog | 0.95 | 0.99 | 1.72 | 1.36 | 1.89 |
| tubulin, beta polypeptide | 0.95 | 0.99 | 1.72 | 1.36 | 1.89 |
| family with sequence similarity 10, member A4 | 1.37 | 1.95 | 1.31 | 2.49 | 2.56 |
| annexin A2 | 1.36 | 3.13 | 2.15 | 1.37 | 1.61 |
| RCD1 required for cell differentiation1 homolog | 2.51 | 0.80 | 5.36 | 2.06 | 6.95 |
| tubulin, beta, 4 | 1.54 | 1.36 | 1.89 | 2.75 | 2.90 |
| ras-related nuclear protein | 1.72 | 1.34 | 2.79 | 2.58 | 3.12 |
| tubulin, beta, 2 | 0.83 | 0.91 | 1.15 | 1.28 | 1.36 |
| mitochondrial ribosomal protein S23 | 1.15 | 1.62 | 0.26 | 2.69 | 1.92 |
| heme binding protein 1 | 0.89 | 0.76 | 1.48 | 1.34 | 1.40 |
| ribosomal protein S3 | 1.35 | 1.94 | 1.32 | 2.14 | 2.04 |

METHOD OF ANALYZING PROTEIN STRUCTURAL AFFINITY RELATIONSHIP

TECHNICAL FIELD

The present invention relates to a method for analyzing a structural affinity relationship between plural kinds of proteins and a compound.

BACKGROUND ART

Genome sequences of human and many other organism have been analyzed, and efficient and logical genome-based drug discovery based on the obtained genomic information now draw attention. Most of the targets of the drugs are proteins. The number of proteins synthesized from human genes is estimated to be about 32,000 in total. Considering the post-translational modifications, the number of such proteins is several times more than the number simply calculated based on the number of human genes. Also considering there are drugs which do not directly act on the humans such as antibiotics, a huge number of proteins are to be analyzed for drug discovery. However, only a limited number of proteins can be actual targets of drugs.

Recently, once a specific target protein is determined for drug discovery, it has become possible to screen an optimum compound for the target among many compounds by a technique such as HTS (High Throughput Screening) or the like. This is now a main style for drug discovery studies. However, specificity (binding, interaction, etc.) of the selected compound has been merely confirmed with respect to several kinds of proteins. No comprehensive review on the specificity has been performed.

Identification of true target molecules of the drug candidates and information transmission paths involving the target molecules clarifies mechanism of drug efficacy and side effects, and thus plays an important role in clinical tests for differentiating the drug of interest from other drugs in efficacy, side effects or the like. There are several techniques for searching for target molecules of drugs, but biochemical experiments are required at a final stage anyway to directly prove the interaction between the drugs and target proteins.

Proteomics has advantages over genetics in that proteins binding to drugs can be directly analyzed with a mass spectrometer (MS) and that the protein samples may be derived from cultured cell or organs.

As a technique for isolating a specific proteins, affinity chromatography is widely used. As a representative example of using affinity chromatography for the purpose of isolating proteins bound to compounds, identification of cis-trans peptidyl-prolyl isomerase (FKBP) as a target protein of immunosuppressant drug FK506, was cited[1,2]. Harding et al. immobilized FK506 to an affinity matrix with the activity being retained, and flowed lysate prepared from spleen. They competitively eluted proteins bound to a ligand with a non-immobilized FK506 solution, and thus obtained FKBP as a specific binding protein. Some physiologically active natural substances strengthen activity thereof by covalently binding to the target[3-5]. A tag such as biotin is introduced into such a substance, and the resultant substance is added to a cell and incubated for a certain time period to prepare lysate. From the obtained lysate, a compound labeled with a biotin tag is collected using a column having avidin immobilized thereon. In this way, the protein bound to the compound can be identified. Sin et al. synthesized a biotinated derivative of fumagillin having an angiogenesis suppressive activity, and reacted the biotinated derivative with the bovine brain extract. After performing several stages of chromatography, they collected the biotinated derivative using an avidin column, and identified type II methionine aminopeptidase (MetAP-2) as a specifically binding protein. Unlike the affinity chromatography with the compound immobilized thereon, this system enable the reaction of a cultured cell, as well as in a cell extract, and a probe under physiological conditions. This is effective for isolating binding proteins which are easily denatured during cell fractionation or lysate preparation[5].

Affinity chromatography may occasionally identify proteins not originally expected[6-9]. Knockaert et al.[7] evaluated various cycline-dependent kinase (CDK) inhibitors, first with an in vitro kinase panel measurement system. The enzymes used were quite limited, mainly several types of CDK and glycogen synthase kinase-$3\alpha/\beta$ (GSK-$3\alpha/\beta$). This assay demonstrated that paullone is an inhibitor against CDK and GSK-$3\alpha/\beta$. When paullone immobilized to an affinity matrix was used as a probe for purifying binding proteins, an unexpected result was obtained. It was found that mitochondrial malate dehydrogenase (mMDH) specifically binds to this probe as well as these types of kinase. In an in vitro enzymatic activity measurement performed thereafter, it was confirmed that paullone inhibits mMDH activity with certainty. A technique using affinity chromatography clarified an unexpected novel intracellular target (mMDH) regarding paullone for the first time in history. This experimental result is considered to provide some suggestions to the studies on targets and action mechanisms of compounds. One of the suggestions is that the action of the compound may possibly be expressed as a total of a plurality of mechanisms, not only as the expected mechanism via the target protein.

Affinity chromatography is based on non-covalent interaction between compounds and proteins except for some physiologically active natural substances. However, when the affinity is weak, a true target may be dissociated from the compound during the operation. For example, a compound may be saturated with a protein having a stronger affinity or a protein having an equal strength of affinity but contained in a larger amount. Namely, proteins obtained by affinity chromatography include a certain amount of proteins bound by non-specific interaction. Especially, a drug having a high protein binding ratio can possibly be bound to a great number of proteins in serum or the like. Such a drug often has 200 to 300 kinds of proteins binding thereto even after, for example, being thoroughly washed with 1 M sodium chloride in an affinity column or the like. Therefore, even though the proteome technology has been developed to make it relatively easy to identify many proteins, how to find specific proteins from these identified proteins is important. Shimizu et al. coated a matrix surface with a highly hydrophilic polymer having a high molecular weight and thus reduced the non-specific adsorption of the matrix as compared to generally used matrices[2].

Another attempt to reduce the non-specific interaction is to narrow a range of a group of proteins which may be specifically bound to the compounds before affinity chromatography is performed[10]. In order to examine proteins bound to chloroquine, which is an anti-malaria drug having a quinoline backbone, a group of ATP-binding proteins are first purified by a column having ATP (adenosine triphosphate) immobilized thereon to obtain a group of binding protein candidates. Quinoline, which has a structure similar to that of purine, is considered to have affinity to proteins bound to purine nucleotides such as ATP and DNA. Therefore, by narrowing a range of targets as target candidates using an ATP column in advance, the non-specific interaction was reduced and thus target proteins of chloroquine were identified. This clarified that chloroquine acts on humans, not on malaria, and thus the action mechanism and the side effect mechanism were estimated.

Another attempt to increase the specificity is to competitively elute binding proteins from a compound-immobilized column, using non-immobilized compounds, molecules which are considered to compete for binding sites (e.g., ATP or NADH (nicotinamide adenine dinucleotide)) or the like. An analysis of proteins bound to p38 inhibitor SB203580 successfully increased the p38 recovery ratio by eluting compounds together with ATP[11]. By this method, a great number of new types of kinase bound to SB203580, which had been considered to p38-specific. Such competitive elution of compounds requires that sufficient amount of the compounds should be dissolved in an aqueous solution, and it is difficult to apply this method to a poorly soluble drug. However, by mixing a non-immobilized, free compound to a protein mixture solution before applied to the affinity column, the target can be masked. A sample containing the masked protein is applied to the affinity column, and column-binding proteins are separated by SDS-PAGE. The bands on the SDS-PAGE are compared based on whether or not the protein is masked or not. The band which disappeared by being masked is considered to be the target[2]. Even a compound having a poor water solubility is expected to be dissolved to a certain degree in a protein mixture solution.

However, compounds having a low molecular weight are mostly bound to serum proteins to some extent. Therefore, target proteins specific to compounds having a low molecular weight need to be found from binding proteins.

This is realized by preparing a compound having a similar structure to that of, but a different activity from that of, the intended compound and performing differential display of binding proteins. SDS-PAGE may be performed to find different bands, but it is not easy to separate all the bands where there are many binding proteins. Under the circumstances, the present inventor reviewed a target protein identification technique for a novel anti-cancer drug E7070 by performing MS analysis[12] using two-dimensional electophoresis or stable isotope labeling, and reported the results[13]. E7070 is a compound screened, using an indication that a cell cycle of a mouse derived cancer cell P388 is inhibited by G1 phase[14]. The binding proteins to E7070 had been unknown. The present inventor attempted to identify the binding proteins using E7070 as an affinity probe. With a technique using a probe, the quality of the probe is a key factor. It is ideal that the probe has about the same degree of activity as that of the original compound. A compound has a structure indispensable to express the activity thereof. The indispensable structure is clarified based on the structural activity relationship while a chemist converts the structure of the compound and improves the activity. A linker is extended from a part which is not the indispensable structural part to introduce the probe to the matrix. With E7070, a probe was synthesized by converting a sulfamoyl group based on the structural activity relationship. Binding proteins were identified by affinity chromatography having E7070 immobilized thereon. However, a huge number of proteins were bound to the probe, and it was difficult to narrow the range of the target proteins. In general, synthetic compounds having a low molecular weight have a low specificity and tend to bind to various proteins. Synthetic compounds having a low molecular weight such as E7070 are often poorly water-soluble, and therefore it is often difficult to specifically elute such compounds by flowing non-immobilized drugs to the affinity column in a huge amount. E7070 was also poor in water solubility, and had to be eluted using a solution such as a surfactant or a denaturing agent increasing the elution capability of the solution step by step. Various purification conditions were reviewed. With E7070, most of the eluted proteins were bound to the compound, and there was no non-specific adsorption to beads or linker. The present inventor newly prepared probes using compounds having a similar structure to, but a different anti-tumor activity from, E7070. The proteins eluted from each of the probes were analyzed using a quantitative proteome technique of ICAT[15, 16] and 2D-DIGE[17] to construct a strategy for identifying proteins strongly adsorbing to E7070[13]. As a result, the present inventor successfully identified proteins highly specifically adsorbing to an E7070 type probe among a great number of proteins adsorbing to the two matrices. Unlike the conventional qualitative determination based on the presence/absence of the band by SDS-PAGE, such a quantitation can provide a highly reliable result.

However, the above-described method still has some problems as exemplified below. (1) Although the compounds need to be immobilized on the carrier (encompassing a carrier filling the column; hereinafter, occasionally referred to simply as "column"), most of the compounds synthesized for screening occasionally cannot be immobilized on the carrier (column). Therefore, there is a need to separately synthesize compounds, which requires a huge amount of time and labor. The type of binding proteins often vary in accordance with the site of the compound immobilized on the carrier (column). (2) When changing the structure of a compound such that the compound can be immobilized on the carrier (column), the activity should not be changed. However, the specificity or affinity is occasionally changed by changing the structure. (3) When performing differential display by changing the compound to be immobilized on the affinity column, it is difficult to select negative compounds (compounds having a relatively weak activity) rather than positive compounds (compounds having a relatively strong activity). Ideally, all the negative compounds are immobilized on the affinity column, but it is not easy in actuality for reason (1). (4) In general, the amount of compounds immobilized on the affinity column is often 0.1 mg to several milligrams with respect to 1 ml of gel, which corresponds to about 1 mM. However, a drug inducing some phenotype of a cell (having activity) shows activity by the order of several micromoles to several nanomoles, sometimes by the order of picomoles. The concentration of the drug exhibiting activity is significantly different from the concentration of the drug immobilized on the column. In general, when a drug is used at a significantly higher concentration than the dose of efficacy, non-specific toxicity is often exhibited. Namely, it is considered that when a high concentration drug is immobilized on the column, an area exhibiting such toxicity may be involved. It is possible to reduce the amount of the compounds immobilized on the column from several micromoles to several nanomoles. However, it is not necessarily easy to control such a tiny amount of immobilization, because if the amount of binding proteins, i.e., the load of the affinity column, is significantly reduced, there is a possibility that the intended proteins may become undetectable with MS. In order to avoid this, the column size may be increased 100 to 1000 times, but such a large size of column is difficult to handle for practical use.

REFERENCE DOCUMENTS

1) M. W. Harding, A. Galat, D. E. Uehling, and S. L. Schreiber, Nature, 341, 758 (1989).
2) N. Shimizu, K. Sugimoto, J. Tang, T. Nishi, I. Sato, M. Hiramoto, S. Aizawa, M. Hatakeyama, R. Ohba, H. Hatori, 3) N. Sin, L. Meng, M. Q. W. Wang, J. J. Wen, W. G. Bommann, and C. M. Crews, Proc. Natl. Acad. Sci. U.S.A, 94, 6099 (1997).
4) E. C. Griffith, Z. Su, B. E. Turk, S. Chen, Y.-H. Chen, Z. Wu, K. Biemann, and J. O. Liu, Chem. Biol., 4, 461 (1997).
5) N. Kudo, N. Matsumori, H. Taoka, D. Fujiwara, E. P. Schreiner, B. Wolff, M. Yoshida, and S. Horinouch, Proc. Natl. Acad. Sci. U.S.A, 96, 9112 (1999).
6) M. Knockaert, N. Gray, E Damiens, Y-T. Chang, P. Grellier, K. Grant, D. Fergusson, J. Mottram, M. Soete, J-F. Dubremetz, K. L. Roch, C. Doering, P. G. Shultz, and L. Meijer, Chem. Biol., 7, 411 (2000).
7) M. Knockaert, K. Wieking, S. Schmitt, M. Leost, K. M. Grant, J. C. Mottram, C. Kunick, and L. Meijer, J. Biol. Chem., 28, 25493 (2002).
8) J. B. Schnier, G Kaur, A. Kaiser, S. F. Stinson, E. A. Sausville, J. Gardner, K. Nishi, E. M. Bradbury, and A. M. Senderowicz, FEBS Lett., 454, 100 (1999).
9) A. Kaiser, K. Nishi, F. A. Gorin, D. A. Walsh, E. M. Bradbury, and J. B. Schnier, Arch. Biochem. Biophys., 386, 179 (2001).
10) P. R. Graves, J. J. Kwiek, P. Fadden, R. Ray, K. Hardeman, A. M. Coley, M. Foley, T. A. Haystead, Mol. Pharmacol. 62, 1364-1372 (2002).
11) K. Godl, J. Wissing, A. Kurtenbach, P. Habenberger, S. Blencke, H. Gutbrod, K. Salassidis, M. Stein-Gerlach, A. Missio, M. Cotten, H. Daub. Proc. Natl. Acad. Sci. U.S.A. 100, 15434-15439 (2003).
12) S. Sechi, Y. Oda, Curr. Opin. Chem. Biol. 7, 70-77 (2003).
13) Y. Oda, T. Owa, T. Sato, B. Boucher, S. Danicls, H. Yamanaka, Y. Shinohara, A. Yokoi, J. Kuromitsu, and T. Nagasu, Anal. Chem., 75, 2159 (2003).
14) T. Owa, H. Yoshino, T. Okauchi, K. Yoshimatsu, Y. Ozawa, N. H. Sugi, T. Nagasu, N, Koyanagi, and K. Kitoh, J. Med. Chem., 42, 3789 (1999).
15) S. P. Gygi, B. Rist, S. A. Gerber, F. Turecek, M. H. Gelb, and R. Aebersold, Nat. Biotechnol, 17, 994 (1999).
16) D. K. Han, J. Eng, H. Zhou, and R. Aebersold, Nat. Biotechnol., 19, 946 (2001).
17) R. Tonge, J. Shaw, B. Middleton, R. Rowlinson, J. Young, E. Hawims, I. Currie, and M. Davison, Proteomics, 1(1), 377 (2001).

DISCLOSURE OF THE INVENTION

The present invention, made in light of such circumstances, has an object of analyzing a structural affinity relationship between plural kinds of proteins and a compound at the same time, simply and efficiently.

In order to attain the above-described object, the present inventors accumulated active studies and as a result, using an affinity chromatography column having a compound immobilized thereon, purified plural kinds of proteins bound to the affinity chromatography column (herein, the term "purification" encompasses separation and/or enrichment). Separately, using an affinity chromatography column having the compound immobilized thereon, the present inventors purified plural kinds of proteins bound to the affinity chromatography column, from isotope-labeled proteins in contact with a compound. The present inventors found that a structural affinity relationship between plural kinds of proteins and a compound is analyzed by: mixing these purified proteins, analyzing the mixed proteins with a mass spectrometer, identifying each protein based on the mass spectrometry information, obtaining the intensity ratio between the labeled peak and non-labeled peak of each protein, and quantitating the affinity ratio of the compound to each protein from the difference in binding ratio based on the presence/absence of the compound. Thus, the present inventors completed the present invention.

The present invention is directed to the following.

(1) A method for analyzing a structural affinity relationship between plural kinds of proteins and a compound, comprising the steps of:
(a) using a compound-immobilized carrier to purify plural kinds of proteins bound to the compound on the carrier from a group of isotope-labeled proteins;
(b) using a compound-immobilized carrier to purify plural kinds of proteins bound to the compound on the carrier from a group of proteins brought into contact with a compound beforehand;
(c) mixing the proteins obtained in step (a) and step (b);
(d) analyzing the mixture obtained in step (c) with mass spectrometry;
(e) identifying each of plural kinds of proteins based on information obtained by the mass spectrometry; and
(f) obtaining, regarding each protein, an intensity ratio between a peak derived from the protein obtained in step (a) and a peak derived from the protein obtained in step (b), thereby quantitating an affinity ratio of the compound to each protein.

(2) A method for analyzing a structural affinity relationship between plural kinds of proteins and a compound, comprising the steps of:
(a) using a compound-immobilized carrier to purify plural kinds of proteins bound to the compound on the carrier, from a group of proteins;
(b) using a compound-immobilized carrier to purify plural kinds of proteins bound to the compound on the carrier from a group of isotope-labeled proteins brought into contact with a compound beforehand;
(c) mixing the proteins obtained in step (a) and step (b);
(d) analyzing the mixture obtained in step (c) with mass spectrometry;
(e) identifying each of plural kinds of proteins based on information obtained by the mass spectrometry; and
(f) obtaining, regarding each protein, an intensity ratio between a peak derived from the protein obtained in step (a) and a peak derived from the protein obtained in step (b), thereby quantitating an affinity ratio of the compound to each protein.

(3) A method for analyzing a structural affinity relationship between plural kinds of proteins and a compound, comprising the steps of:
(a) using a compound-immobilized carrier to purify plural kinds of proteins bound to the compound on the carrier, from a group of proteins;
(b) using a compound-immobilized carrier to purify plural kinds of proteins bound to the compound on the carrier, from a group of proteins brought into contact with a compound beforehand;
(c) isotope-labeling the proteins obtained in either step (a) or step (b);
(d) mixing the labeled proteins obtained in step (c) with the proteins obtained in either step (a) or step (b) which are not labeled in step (c);
(e) analyzing the mixture obtained in step (d) with mass spectrometry;
(f) identifying each of plural kinds of proteins based on information obtained by the mass spectrometry; and (g) obtaining, regarding each protein, an intensity ratio between a peak derived from the protein obtained in step (a) and a peak derived from the protein obtained in step (b), thereby quantitating an affinity ratio of the compound to each protein.

(4) A method for analyzing a structural affinity relationship between plural kinds of proteins and a compound, comprising the steps of:
(a) using a compound-immobilized carrier to purify plural kinds of proteins bound to the compound on the carrier, from a group of proteins;
(b) mixing the proteins obtained in step (a) and a group of isotope-labeled proteins as an internal standard substance;
(c) analyzing the mixture obtained in step (b) with mass spectrometry;
(d) using a compound-immobilized carrier to purify plural kinds of proteins bound to the compound on the carrier, from a group of proteins brought into contact with a compound beforehand;
(e) mixing the proteins obtained in step (d) and a group of isotope-labeled proteins as an internal standard substance;
(f) analyzing the mixture obtained in step (e) with mass spectrometry;
(g) identifying each of plural kinds of proteins based on information obtained by the mass spectrometry in steps (c) and (f); and
(h) obtaining, regarding each protein, an intensity ratio between a peak derived from the protein obtained in step (a) and a peak derived from the protein as an internal standard substance, and an intensity ratio between a peak derived from the protein obtained in step (d) and a peak derived from the protein as an internal standard substance, and comparing the two intensity ratios, thereby quantitating an affinity ratio of the compound to each protein.

(5) A method for analyzing a structural affinity relationship between plural kinds of proteins and a compound, comprising the steps of:
(a1) using a compound-immobilized carrier to purify plural kinds of proteins bound to the compound on the carrier, from a group of proteins;
(a2) analyzing the purified proteins obtained in step (a1) with mass spectrometry;
(a3) identifying each of plural kinds of proteins based on information obtained by the mass spectrometry in step (a2);
(a4) quantitating each of the plural kinds of proteins;
(b1) using a compound-immobilized carrier to purify plural kinds of proteins bound to the compound on the carrier, from a group of proteins brought into contact with a compound beforehand;
(b2) analyzing the purified proteins obtained in step (b1) with mass spectrometry;
(b3) identifying each of plural kinds of proteins based on information obtained by the mass spectrometry in step (b2);
(b4) quantitating each of the plural kinds of proteins; and
(c) obtaining, regarding each protein, a ratio between an amount of the protein obtained in step (a1) and an amount of the protein obtained in step (b1), thereby quantitating an affinity ratio of the compound to each protein.

(6) The method according to any one of (1) through (5), wherein the compound-immobilized carrier is a carrier for affinity chromatography.

(7) The method according to any one of (1) through (3), wherein the contact of the group of proteins with the compound in step (b) is brought into for plural kinds of compounds.

(8) The method according to (4), wherein the contact of the group of proteins with the compound in step (d) is brought into for plural kinds of compounds.

(9) The method according to (5), wherein the contact of the group of proteins with the compound in step (b1) is brought into for plural kinds of compounds.

(10) The method according to any one of (1) through (9), wherein the compound immobilized on the carrier is a compound selected from the group consisting of ATP, GTP, NAD and NADP.

(11) The method according to any one of (1) through (4), (6) through (8) and (10), wherein the isotope is an isotope selected from the group consisting of $^2$H, $^{13}$C, $^{15}$N, $^{17}$O, $^{18}$O, $^{33}$P and $^{34}$S or a combination thereof.

(12) The method according to (11), wherein the isotope is $^{13}$C.

(13) A system for analyzing a structural affinity relationship between plural kinds of proteins and a compound, comprising:
(a) means for using a compound-immobilized carrier to purify plural kinds of proteins bound to the compound on the carrier, from a group of isotope-labeled proteins;
(b) means for using a compound-immobilized carrier to purify plural kinds of proteins bound to the compound on the carrier, from a group of proteins brought into contact with a compound beforehand;
(c) means for mixing the proteins obtained by means (a) and means (b);
(d) means for analyzing the mixture obtained by means (c) with mass spectrometry;
(e) means for identifying each of plural kinds of proteins based on information obtained by the mass spectrometry; and
(f) means for obtaining, regarding each protein, an intensity ratio between a peak derived from the protein obtained by means (a) and a peak derived from the protein obtained by means (b), thereby quantitating an affinity ratio of the compound to each protein.

(14) A system for analyzing a structural affinity relationship between plural kinds of proteins and a compound, comprising:
(a) means for using a compound-immobilized carrier to purify plural kinds of proteins bound to the compound on the carrier, from a group of proteins;
(b) means for using a compound-immobilized carrier to purify plural kinds of proteins bound to the compound on the carrier, from a group of isotope-labeled proteins brought into contact with a compound beforehand;
(c) means for mixing the proteins obtained by means (a) and means (b);
(d) means for analyzing the mixture obtained by means (c) with mass spectrometry;
(e) means for identifying each of plural kinds of proteins based on information obtained by the mass spectrometry; and
(f) means for obtaining, regarding each protein, an intensity ratio between a peak derived from the protein obtained by means (a) and a peak derived from the protein obtained by means (b), thereby quantitating an affinity ratio of the compound to each protein.

(15) A system for analyzing a structural affinity relationship between plural kinds of proteins and a compound, comprising:
(a) means for using a compound-immobilized carrier to purify plural kinds of proteins bound to the compound on the carrier, from a group of proteins;

(b) means for using a compound-immobilized carrier to purify plural kinds of proteins bound to the compound on the carrier, from a group of proteins brought into contact with a compound beforehand;
(c) means for isotope-labeling the proteins obtained by either means (a) or means (b);
(d) means for mixing the labeled proteins obtained by means (c) with the proteins obtained by either means (a) or means (b) which are not labeled by means (c);
(e) means for analyzing the mixture obtained by means (d) with mass spectrometry;
(f) means for identifying each of plural kinds of proteins based on information obtained by the mass spectrometry; and
(g) means for obtaining, regarding each protein, an intensity ratio between a peak derived from the protein obtained by means (a) and a peak derived from the protein obtained by means (b), thereby quantitating an affinity ratio of the compound to each protein.
(16) A system for analyzing a structural affinity relationship between plural kinds of proteins and a compound, comprising:
(a) means for using a compound-immobilized carrier to purify plural kinds of proteins bound to the compound on the carrier, from a group of proteins;
(b) means for mixing the proteins obtained by means (a) and a group of isotope-labeled proteins as an internal standard substance;
(c) means for analyzing the mixture obtained by means (b) with mass spectrometry;
(d) means for using a compound-immobilized carrier to purify plural kinds of proteins bound to the compound on the carrier, from a group of proteins brought into contact with a compound beforehand;
(e) means for mixing the proteins obtained by means (d) and a group of isotope-labeled proteins as an internal standard substance;
(f) means for analyzing the mixture obtained by means (e) with mass spectrometry;
(g) means for identifying each of plural kinds of proteins based on information obtained by the mass spectrometry by means (c) and (f); and
(h) means for obtaining, regarding each protein, an intensity ratio between a peak derived from the protein obtained by means (a) and a peak derived from the protein as an internal standard substance, and an intensity ratio between a peak derived from the protein obtained by means (d) and a peak derived from the protein as an internal standard substance, and comparing the two intensity ratios, thereby quantitating an affinity ratio of the compound to each protein.
(17) A system for analyzing a structural affinity relationship between plural kinds of proteins and a compound, comprising:
(a1) means for using a compound-immobilized carrier to purify plural kinds of proteins bound to the compound on the carrier, from a group of proteins;
(a2) means for analyzing the purified proteins obtained by means (a1) with mass spectrometry;
(a3) means for identifying each of plural kinds of proteins based on information obtained by the mass spectrometry by means (a2);
(a4) means for quantitating each of the plural kinds of proteins;
(b1) means for using a compound-immobilized carrier to purify plural kinds of proteins bound to the compound on the carrier, from a group of proteins brought into contact with a compound beforehand;
(b2) means for analyzing the purified proteins obtained by means (b1) with mass spectrometry;
(b3) means for identifying each of plural kinds of proteins based on information obtained by the mass spectrometry by means (b2);
(b4) means for quantitating each of the plural kinds of proteins; and
(c) means for obtaining, regarding each protein, a ratio between an amount of the protein obtained by means (a1) and an amount of the protein obtained by means (b1), thereby quantitating an affinity ratio of the compound to each protein.
(18) The system according to any one of (13) through (17), wherein the compound-immobilized carrier is a carrier for affinity chromatography.
(19) The system according to any one of (13) through (15), wherein the contact of the group of proteins with the compound by means (b) is brought into for plural kinds of compounds.
(20) The system according to (16), wherein the contact of the group of proteins with the compound by means (d) is brought into for plural kinds of compounds.
(21) The system according to (17), wherein the contact of the group of proteins with the compound by means (b1) is brought into for plural kinds of compounds.
(22) The system according to any one of (13) through (21), wherein the compound immobilized on the carrier is a compound selected from the group consisting of ATP, GTP, NAD and NADP.
(23) The system according to any one of (13) through (16), (18) through (20) and (22), wherein the isotope is an isotope selected from the group consisting of $^2$H, $^{13}$C, $^{15}$N, $^{17}$O, $^{18}$O, $^{33}$P and $^{34}$S or a combination thereof.
(24) The system according to (23), wherein the isotope is $^{13}$C.

According to the present invention, a structural affinity relationship between plural kinds of proteins and a compound can be analyzed at the same time, simply and efficiently.

According to the present invention, it is not necessary any more to prepare a plurality of affinity chromatography columns having a compound immobilized thereon. Information on the structural affinity relationship based on a plurality of compounds can be obtained simply and efficiently. According to the present invention, only one of the compounds is immobilized and the other compounds are used without being immobilized. Therefore, the affinity of each compound to the protein can be evaluated while the original structure of each compound is maintained. Thus, more accurate information on the structural affinity relationship is made available.

According to the present invention, compounds of various structures can be used by changing the structure of the compounds. Therefore, how the structure of a compound influences the affinity to the protein can be comprehensively analyzed. Thus, the structural affinity relationship between compounds and proteins can be comprehensively analyzed. As a result, information useful for synthesizing and developing compounds, especially drugs, which enhance main actions while reducing side effects is made available.

According to the present invention, as a compound to be immobilized on the carrier, ATP, GTP (guanosine triphosphate), NAD/NADH (nicotinamide adenine dinucleotide), or NADP/NADPH (nicotineamide dinucleotide phosphate) is used. Thus, information on the structural affinity relationship between plural kinds of proteins bound to ATP, GTP, NAD or NADP and a compound is made available.

Practically, according to the present invention, information on the structural affinity relationship is made available using a carrier having ATP immobilized thereon. Thus, it is made possible to conduct a comprehensive analysis on the affinity with what type of kinase is influenced by a structural change of a compound. This provides information on specificity and selectivity which is useful for screening kinase inhibitors.

According to the present invention, information on the structural affinity relationship is made available using a carrier having GTP immobilized thereon. Thus, it is made possible to conduct a comprehensive analysis on the affinity with what type of GTP-binding proteins is influenced by a structural change of a compound. This provides information on specificity and selectivity which is useful for screening GTP-binding protein inhibitors.

According to the present invention, information on the structural affinity relationship is made available using a carrier having NAD or NADP immobilized thereon. Thus, it is made possible to conduct a comprehensive analysis on the affinity of what type of dehydrogenase is influenced by a structural change of a compound. This provides information on specificity and selectivity which is useful for screening dehydrogenase inhibitors.

A compound immobilized on the carrier (e.g., an affinity chromatography column) generally has a concentration of about 0.1 mg to several milligrams with respect to 1 ml of carrier, which corresponds to about 1 mM. However, it is known that a compound having some activity on a cell exhibits the activity by the order of several micromoles to several nanomoles, or sometimes by the order of several picomoles. The concentration of a compound exhibiting some activity on a cell is significantly different from a concentration of the compound immobilized on the carrier (e.g., an affinity chromatography column). According to the present invention, compounds are used without being immobilized on the carrier. This makes it possible to reduce the concentration of the compound from several micromoles to several nanomoles.

BRIEF DESCRIPTION OF THE DRAWINGS

FIG. 5 shows a structural affinity relationship between plural kinds of proteins and compounds represented by formulas 2 through 6 (chemical formulas 2 through 6). A smaller numerical value represents a stronger affinity to the compound.

DESCRIPTION OF THE REFERENCE NUMERALS

Figure 1:
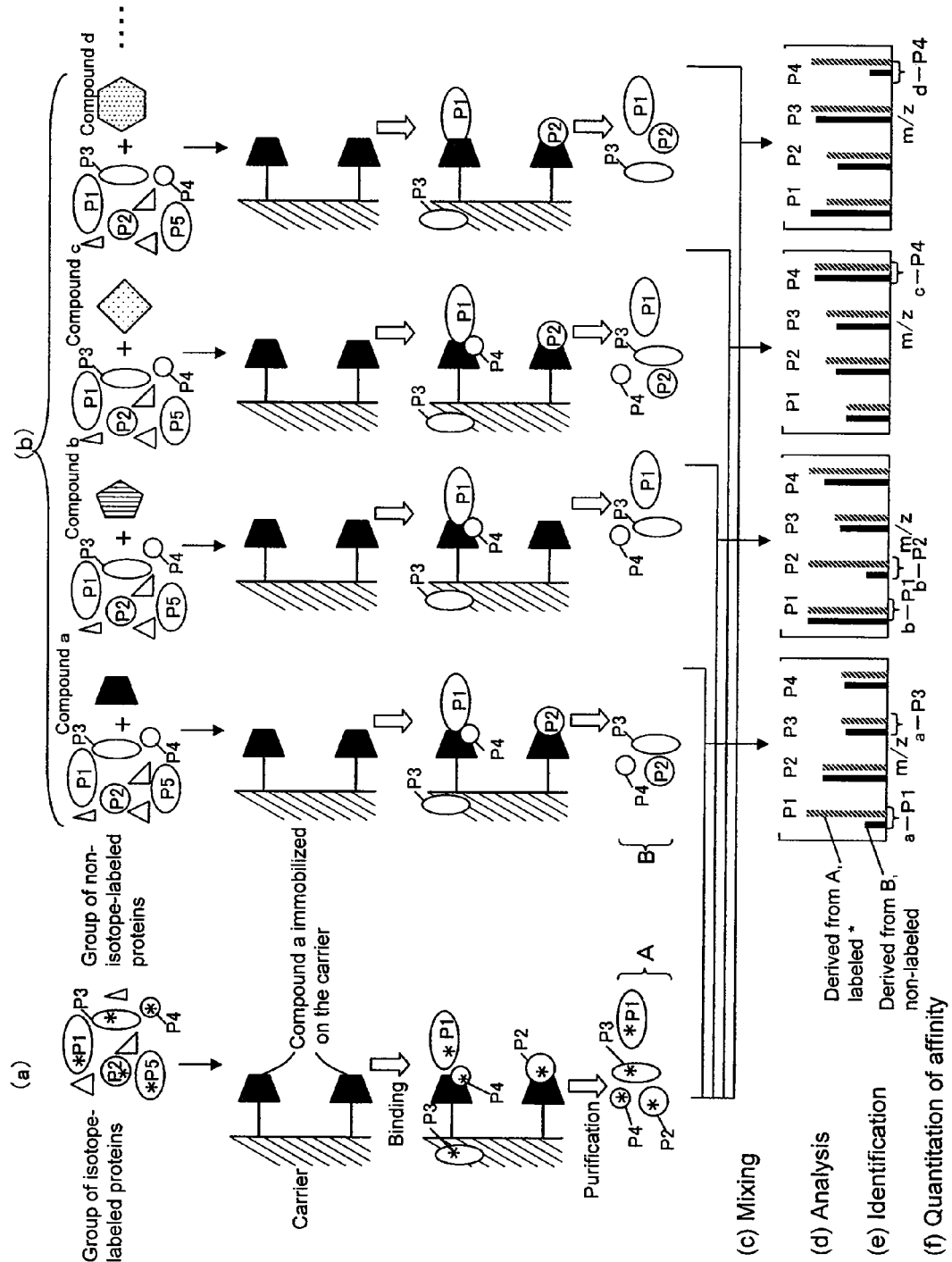
FIG. 1 schematically shows a first embodiment of the present invention.

1a: tube
1b: tube
2a: stirring blade
2b: stirring blade
11a: culture device
11b: culture device
11c: culture device
12a: culture liquid bottle
12b: culture liquid bottle
13a: cell crushing device
13b: cell crushing device
13c: cell crushing device
14: compound contact device
14c-1: compound contact device
14c-2: compound contact device
14c-3: compound contact device
15a: compound-immobilized carrier
15b: compound-immobilized carrier
16a: protein purification control device
16b: protein purification control device
17a: purified protein separator
17b: purified protein separator
18: tube
19: plate
20: mass spectrometer
21: computer
30: central computer
31: sample divider
100: LAN
601: control unit
602: protein purification unit
603: protein mixing unit
604: mass spectrometry unit
801: CPU
802: transmission/receiving section
803: input section
804: output section
805: ROM
806: RAM
807: hard disc drive (HDD)
808: CD-ROM drive
809: protein database (DB)
810: CD-ROM
811: Internet

BEST MODE FOR CARRYING OUT THE INVENTION

Hereinafter, embodiments of the present invention will be described. The following embodiments are given in order to illustrate the present invention and are not intended to limit the present invention in any way. The present invention can be carried out in various embodiments without departing from the scope thereof.

The documents, laid-open publications, patents and other patent documents cited in this specification are incorporated herein by reference.

The present invention relates to a method for analyzing a structural affinity relationship between plural kinds of proteins and at least one kind of compound. The method according to the present invention is based on (i) purifying proteins using a carrier having a compound immobilized thereon, (ii) separately bringing proteins into contact with a compound and purifying the proteins in contact using the carrier; and (iii) measuring the quantity ratio between proteins purified in (i) and (ii) by mass spectrometry using isotope labeling or indicator EMPAI.

An example of the above-described method is carried out as follows. First, using a carrier (column) having a compound immobilized thereon, plural kinds of proteins bound to the compound on the column are purified from a group of isotope-labeled proteins. Separately, using the carrier (column) having a compound immobilized thereon, plural kinds of proteins bound to the compound on the column are purified from a group of non-isotope-labeled proteins or a group of different-isotope-labeled proteins brought into contact with at least one type of compound beforehand.

The proteins to be added to the carrier (column) (e.g., proteins extracted from a cell) include various kinds of proteins existing in various manners. A method according to the present invention uses a carrier (column) to select plural kinds of proteins bound to the compound on the carrier (column) as a target of the subsequent analysis. Namely, the method according to the present invention selects plural kinds of proteins having a similar nature of binding to the compound, from a group of proteins which include various kinds of proteins as a population, and analyzes a structural affinity relationship between the plural kinds of proteins and at least one kind of compound.

Also according to the present invention, a group of proteins as a population are brought into contact with a compound beforehand. Then, using a carrier (column), plural kinds of proteins bound to the compound on the carrier are purified from the proteins. A part of the proteins are difficult to bind to the compound on the carrier (column) because the binding sites compete with the compound bound to the proteins beforehand. As a result, the amount of proteins purified from the column (defined as (cc)) is smaller than the amount of proteins purified from the column without being brought into contact with the compound beforehand (defined as (c)). By isotope-labeling either proteins, (c) and (cc) can be compared at the same time by mass spectrometry, and thus the affinity ratio can be calculated. The present invention uses this principle to analyze the structural affinity relationship between plural kinds of proteins and at least one type of compound.

In the present invention, the term "structural affinity relationship" refers to the relationship between a structural change of a group of chemical substances having a common backbone structure and the affinity (binding strength) of the chemical substances with a protein.

In the present invention, the term "protein" encompasses a peptide including two or more amino acids bound together by peptide binding.

<Compound-Immobilized Carrier>

In the present invention, the expression "compound-immobilized carrier" refers to a carrier having a compound covalently or noncovalently bound thereto via a functional group.

A compound-immobilized carrier is obtained, for example, as follows. First, N-hydroxy-succinimide or hydrazide as a functional group is covalently bound to the carrier; simply an amino group is introduced to the carrier; or Protein A, heparin, Cibacron Blue F3GA or the like is immobilized on the carrier. Then, a compound is covalently or noncovalently bound to such a carrier, with or without a partial structural change.

There is no specific limitation on the compound to be immobilized on the carrier. Usable compounds include, for example, synthesized compounds having a low molecular weight, synthesized peptides, purified or partially purified polypeptides, antibodies, released substances from bacteria (including bacterial metabolite), intravital nucleic acid substances (e.g., ATP, GTP, NAD/NADH, or NADP/NADPH), and lipid. Such a compound may be a novel compound or a known compound. A compound to be immobilized on the carrier has a predefined activity. Herein, the expression "predefined activity" refers to an activity owned by a compound immobilized on the carrier or a non-immobilized compound described later, with no specific limitation. A "predefined activity" may be, for example, physiological activity, biological activity, pharmacological activity, or binding activity.

Usable carriers include, for example, agarose gel, acrylamide, magnetic bead, cellulose, and silica gel. Agarose gel is preferable. Such a carrier is available from, for example, BioRad (Affi-gel 10, produced by BioRad, Cat. No. 153-6099).

A compound-immobilized carrier may be produced by binding a desired compound to the carrier. A carrier having, for example, a compound containing an amino group immobilized thereon may be produced as follows. First, a compound solution containing an amino group is added to a carrier having N-hydroxy-succinimide binding thereto (e.g., Affi-gel 10). Next, triethylamine is added thereto and incubated. Then, 2-aminoethanol is added thereto and further incubated. Thus, a carrier having a compound containing an amino group immobilized thereon is produced. It is preferable to perform a washing operation when necessary.

A carrier having, for example, a compound having carboxylic acid immobilized thereon may be produced as follows. First, carbodiamide is added to a compound solution containing carboxylic acid, and incubated. The resultant substance is added to a carrier having an amino group binding thereto. Next, acetic acid (or lactic acid) is added and incubated again. Thus, a carrier having a compound containing carboxylic acid immobilized thereon is produced. It is preferable to perform a washing operation when necessary. A carrier having an NADP analog immobilized thereon is available from, for example, Amersham Biosciences (2'5'ADP Sepharose 4B (code number: 17-0700-01)).

There is no specific limitation on the amount of the compound to be immobilized on the carrier. A preferable amount is 0.1 mg to several milligrams per 1 ml of carrier.

A compound-immobilized carrier can be used for affinity chromatography. When an appropriate column (e.g., Polyprep empty column (produced by BioRad, Cat No. 731-1550)) is filled with such a carrier, the carrier can be used as an affinity chromatography column having a compound immobilized thereon. Such a carrier can also be used when being put into an appropriate tube (e.g., Eppendorf tube (produced by Eppendorf)).

1. First Embodiment of the Present Invention

A first embodiment of the present invention provides a method for analyzing a structural affinity relationship between plural kinds of proteins and a compound, comprising the steps of:
(a) using a compound-immobilized carrier to purify plural kinds of proteins bound to the compound on the carrier, from a group of isotope-labeled proteins;
(b) using a compound-immobilized carrier to purify plural kinds of proteins bound to the compound on the carrier, from a group of proteins brought into contact with a compound beforehand;
(c) mixing the proteins obtained in step (a) and step (b);
(d) analyzing the mixture obtained in step (c) with mass spectrometry;
(e) identifying each of plural kinds of proteins based on information obtained by the mass spectrometry;
(f) obtaining, regarding each protein, an intensity ratio between a peak derived from the protein obtained in step (a) and a peak derived from the protein obtained in step (b), thereby quantitating an affinity ratio of the compound to each protein.

The first embodiment of the present invention will be briefly described (see FIG. 1).

According to the present invention, first, a carrier having a compound having a predefined activity immobilized thereon (e.g., an affinity chromatography column) is provided. The amount of the compound having the activity to be immobilized is preferably 0.1 mg to several milligrams per 1 ml of carrier. To this compound-immobilized carrier, a group of proteins (in FIG. 1(a), represented with triangles, circles and ellipses) labeled with isotopes (in FIG. 1, represented with "*") are applied. Then, proteins bound to the compound (in FIG. 1(a), represented with circles and ellipses) are purified. An group of the obtained plurality of kinds of proteins are referred to as "protein A" (FIG. 1(a)). Here, the expression "group of proteins" refers to a sample as a population to be put on the carrier (applied).

Compounds which are not immobilized on the carrier (one or plural kinds of compounds having a predefined activity; it is preferable that the strength of the activity is different among the compounds) (in FIG. 1(b), compounds a, b, c, and d) are each added to a group of non-isotope-labeled proteins (in FIG. 1(b), represented with triangles, circles and ellipses) so as to have an appropriate concentration (e.g., several micromoles) and incubated for a predetermined time period, thereby bringing the group of proteins and the compound into contact with each other (sample solution). Herein, a compound which is added to be brought into contact with the group of proteins and is not immobilized will be occasionally referred to as a "non-immobilized compound". This sample solution contains a great amount of proteins. Therefore, even a compound which is poorly water-soluble can be dissolved in the sample solution to some extent. Instead of the group of non-isotope-labeled proteins, a group of proteins labeled with an isotope different from the isotope in the "group of isotope-labeled proteins" mentioned above are usable.

Each sample solution is put on a carrier having the compound having the predefined activity immobilized thereon, and proteins bound to the compound are purified. An group of the obtained plurality of kinds of proteins are referred to as "protein B". Since a sample solution is prepared for each type of non-immobilized compound, the number of kinds of proteins B matches the number of kinds of non-immobilized compounds (FIG. 1(b)). In FIG. 1(b), four non-immobilized compounds (compounds a, b, c, and d) are brought into contact with the proteins beforehand. Thus, there are four kinds of proteins B.

Protein A and protein B are mixed at a certain ratio (FIG. 1(c)). The proteins are separated by SDS-PAGE or the like, then digested by trypsin or the like, and treated with mass spectrometry (FIG. 1(d)). Then, the proteins are identified (FIG. 1(e)). Mass spectra obtained as a result of the mass spectrometry (FIG. 1(d)) exhibit peaks in pairs, i.e., a peak of protein A derived from the isotope-labeled sample (dashed line peak) and a peak of protein B derived from the non-isotope-labeled sample (black solid line peak). For each protein, the intensity ratio between the peak derived from protein A and the peak derived from protein B is obtained. Thus, the affinity of the compound to each protein is quantitated (FIG. 1(f)).

Hereinafter, an example of analysis when protein A and protein B are mixed at a ratio of 1:1 will be described.

A protein bound to the non-immobilized compound (e.g., compound b in FIG. 1) is less likely to be bound to compound a immobilized on the carrier. Therefore, the mass spectra exhibit that the peak derived from protein B is smaller than the peak derived from protein A. For example, it is assumed that a site of a protein of protein B (e.g., protein P2 in FIG. 1) bound to compound a and the site of the protein of protein B (e.g., protein P2 in FIG. 1) bound to compound b are the same or overlapping, and further the affinity of compound b to protein P2 is higher than the affinity of compound a to protein P2, or the concentration of compound b is higher than the concentration of compound a. In this case, the binding site is used for compound b. Therefore, protein P2 is less likely to bind to compound a immobilized on the carrier. As a result, the amount of protein P2 of protein B purified from the carrier is smaller than the amount of protein P2 of protein A purified from the carrier. This is why the mass spectrum peak derived from protein B is smaller than the mass spectrum peak derived from protein A (FIG. 1, b-P2). When the binding site of protein P2 with compound a is masked by protein P2 bound being compound b, substantially the same phenomenon occurs.

By contrast, the protein (e.g., protein P1 in FIG. 1) which is not bound to the non-immobilized compound added later (e.g., compound b in FIG. 1) is not influenced by the binding thereof to the compound immobilized on the carrier. Therefore, the substantial amount of protein P1 bound to the compound on the carrier is the same regardless of whether the non-immobilized compound is added or not. Here, the term "substantial" refers to the amount obtained without considering the change in the non-specific binding amount of the protein to the compound immobilized on the carrier. Such a change occurs by the addition of the non-immobilized compound. Therefore, the peak of protein P1 of protein B is substantially the same as the peak of protein P1 of protein A (FIG. 1, b-P1) with no difference in the peak intensity.

When the non-immobilized compound added later is the same as the compound immobilized on the carrier (e.g., compound a in FIG. 1), compound a immobilized on the carrier is competitively inhibited from binding to the protein (e.g., protein P1) by non-immobilized compound a. Therefore, the amount of the protein bound to compound a immobilized on the carrier is reduced. As a result, when protein A and protein B both obtained by purification are mixed at a ratio of 1:1, the mass spectra exhibit that the peak derived from non-labeled protein B is smaller than the peak derived from labeled protein A (FIG. 1, a-P1).

Even when the non-immobilized compound added later is the same as the compound immobilized on the carrier, and purified proteins A and B are mixed at a ratio of 1:1, the mass spectra may exhibit that the peak derived from protein B is not smaller than the peak derived from protein A regarding a certain type of protein (FIG. 1, a-P3). It is appreciated that a protein showing such a peak pattern is a non-specific binding protein which is bound to a part other than the compound (e.g., a part of the carrier).

In a comparison among non-immobilized compounds having different activities (e.g., compounds a, b, c and d in FIG. 1), the mass spectra may exhibit that the peak of a certain protein of protein B is smaller than the peak of the same protein of protein A by about the same amount (e.g., protein P3 in FIG. 1). Such a protein is considered not to be a specific binding protein which is important to the activity of any of added compounds a, b, c and d.

Even when a non-immobilized compound having a predefined activity (e.g., compound d in FIG. 1) has a low concentration, the mass spectra may exhibit that the peak derived from protein B is small (FIG. 1, d-P4). Such a protein (e.g., protein P4 in FIG. 1) may possibly be important to the activity of the compound. Similarly, when the peak derived from protein B is not influenced in mass spectra by another non-immobilized compound having a similar structure but a different activity (e.g., compound c in FIG. 1) (FIG. 1, c-P4), there is a high possibility that protein P4 is a specific binding protein which is important to the activity of non-immobilized compound d.

When the affinity between a non-immobilized compound and a protein is very weak (it is not known how weak) and the concentration of the compound is low, the compound bound to the protein may possibly be replaced with a compound immobilized to the column at a high concentration while the compound passes through the column. Such an influence may be lowered by increasing the concentration of the non-immobilized compound.

With the above-described method, a structural affinity relationship between a plurality of proteins and a compound can be analyzed at the same time, simply and efficiently.

A compound-immobilized carrier (e.g., an affinity chromatography column) may be a carrier or column having ATP, GTP, NAD/NADH, NADP/NADPH or the like immobilized thereon. By examining the affinity with various compounds in a similar manner using such a carrier or column, a structural affinity relationship between a compound bound to an ATP, GTP, NAD/NADH or NADP/NADPH binding site of a specific protein and such a protein can be found.

This method uses an isotope. Therefore, quantitative information can be obtained by calculating the peak intensity ratio in the mass spectra, in addition to based on the presence/absence of the band on the SDS-PAGE. Such information is important to researchers in the field of compound synthesis. Conventionally, a structural affinity relationship is analyzed by examining an activity value of a compound with respect to one target molecule or one assay system while varying the compound. In this manner, it was determined what compounds should be synthesize next. With the method according to the present invention, a structural affinity relationship between one or plural kinds of compounds and plural kinds of proteins can be comprehensively analyzed. Namely, from the viewpoint of one compound, the difference in specificity with respect to the plural kinds of proteins bindable to the compound can be quantitatively evaluated. From the viewpoint of one protein, the difference in binding with respect to the plural kinds of compounds can be quantitatively checked.

Hereinafter, the first embodiment of the present invention will be described in detail.

<Group of Isotope-Labeled Proteins and Group of Non-Isotope-Labeled Proteins>

Herein, the expression "group of isotope-labeled proteins" refers to an assembly of proteins in which a part of the molecules are labeled with an isotope.

A group of isotope-labeled proteins may be an assembly of any proteins in which a part of the molecules (amino acids) is labeled with an isotope. There is no specific limitation on the method for preparation or labeling site.

Hereinafter, a practical method for preparing a group of isotope-labeled proteins will be described.

A group of isotope-labeled proteins may be prepared by metabolic isotope labeling. For example, proteins in a cell may be metabolically isotope-labeled by culturing a culturable cell in a medium containing an isotope-labeled amino acid. Any culturing condition is usable. A medium preferable to culture the cell in a liquid medium or a solid medium may be selected. For example, when an animal cell is selected, a medium such as DMEM, MEM, RPMI1640, IMDM or the like may be used. When necessary, serum such as fetal calf serum (FCS) or the like, amino acid, glucose, penicillin, streptomycin or the like may be added. Culturing can be performed at a pH of about 6 to 8 and 30 to 40° C. for around 15 to 200 hours. When necessary, the medium may be changed, or ventilation or stirring may be performed.

A cell containing a group of proteins metabolically isotope-labeled thus obtained is crushed, thereby preparing a group of isotope-labeled proteins. A method for crushing may be a method using a Downs-type TEFLON® polytetrafluoroethylene homogenizer, a polytron, a warring blender, a Potter-type glass homogenizer, an ultrasonic crushing device or a cell-dissolved solution (e.g., M-PER: Cat No. 78501, T-PER: Cat No. 78510, both produced by PIERCE), or a freezing and thawing method. A method using a cell-dissolved solution is preferable. The crushed cell is preferably deprived of insoluble substances by centrifugation. In this way, a group of isotope-labeled proteins can be prepared.

An isotope used in the present invention may be a radioactive isotope, but a stable isotope with no radioactivity is easy to handle and especially preferable. Usable stable isotope include, with no limitation, $^2H$, $^{13}C$, $^{15}N$, $^{17}O$, $^{18}O$, $^{33}P$, $^{34}S$ or a combination thereof. $^2H$, $^{13}C$, $^{15}N$, or $^{18}O$ or a combination thereof is preferable; $^{13}C$, $^{15}N$, or $^{18}O$ or a combination thereof is more preferable; and $^{13}C$ is especially preferable. According to the present invention, any type of isotope which can label a protein is usable with no specific limitation. Practically, $^{13}C$ label ($^{13}C \times 6$) leucine (produced by Cambridge Isotope Labs (CIL), L-Leucine U-$^{13}C6$, CLM-2262) is usable as a precursor of an isotope-labeled protein.

A group of isotope-labeled proteins may also be prepared in vitro. For example, the proteins may be isotope-labeled by alkylating cysteine residue in the proteins using an isotope-labeled alkylating reagent (see Rapid Communications in Mass Spectroscopy, Vol. 16, No. 15 (2002), pp. 1416-1424). Alternatively, the proteins may be isotope-labeled by biotinylating cysteine residue in the proteins using an isotope-labeled biotinylating reagent. Using an adipin column, only the labeled proteins may be purified (Nature Biotechnology, Vol. 17, No. 10, October 1999, pp. 994-999).

In the present invention, the expression "group of non-isotope-labeled proteins" refers to an assembly of proteins not treated with isotope labeling.

A group of non-isotope-labeled proteins may be prepared by crushing a biological sample containing proteins, preferably a cell, especially preferably a cultured cell, and extracting the proteins.

A method for crushing may be a method using a Downs-type TEFLON® polytetrafluoroethylene homogenizer, a polytron, a warring blender, a Potter-type glass homogenizer, an ultrasonic crushing device or a cell-dissolved solution (e.g., M-PER: Cat No. 78501, T-PER: Cat No. 78510, both produced by PIERCE), or a freezing and thawing method. A method using a cell-dissolved solution is preferable. The crushed cell is preferably deprived of insoluble substances by centrifugation. In this way, a group of non-isotope-labeled proteins can be prepared.

Alternatively, a group of isotope-labeled proteins and a group of non-isotope-labeled proteins may be prepared by chemical synthesis.

A group of isotope-labeled proteins and a group of non-isotope-labeled proteins may be stored under an appropriate condition, preferably at −20° C. or lower, especially preferably at −80° C. or lower.

In the present invention, a "group of non-isotope-labeled proteins" is preferably prepared by the same method as the "group of isotope-labeled proteins" using a naturally-occurring reagent (non-isotope reagent).

According to the present invention, instead of the "group of non-isotope-labeled proteins", a group of proteins labeled with an isotope different from the isotope in the "group of isotope-labeled proteins" (hereinafter, referred to also as a "group of different-isotope-labeled proteins") are usable. The isotope in the "group of different-isotope-labeled proteins" may be different from the isotope in the "group of isotope-labeled proteins" or may include the same isotope, as long as the proteins can be labeled such that the mass of each type of protein is different between the two kinds of protein groups.

(1)(a) Step of Using a Compound-Immobilized Carrier to Purify Plural Kinds of Proteins Bound to the Compound on the Carrier, from a Group of Isotope-Labeled Proteins A group of isotope-labeled proteins are purified using a compound-immobilized carrier. By this, plural kinds of proteins bound to the compound immobilized on the carrier can be purified. Herein, "using a carrier" refers to using a compound-immobilized carrier when purifying a group of proteins as a population.

Hereinafter, this will be described in detail.

First, a compound-immobilized carrier is equilibrated with an appropriate solution. The solution for equilibration is not specifically limited, but preferably can dissolve proteins and does not denature the proteins. For example, a phosphoric acid buffer solution, a Hepes buffer solution, or Tris buffer solution, each prepared to have a physiological pH value, is usable. When necessary, sodium chloride and/or a surfactant (e.g., n-octylglucoside) may be added thereto in an appropriate amount.

In the case where an appropriate column is filled with the compound-immobilized carrier, the step of equilibration may be performed by applying an appropriate solution to the column. In the case where the compound-immobilized carrier is put to an appropriate tube, the step of equilibration may be performed by applying an appropriate solution to the tube.

Next, the group of isotope-labeled proteins are dissolved in an appropriate solution. Then, the group of isotope-labeled proteins, and the compound-immobilized carrier, are brought into contact with each other. In the case where an appropriate column is filled with the compound-immobilized carrier, the step of bringing the group of isotope-labeled proteins, and the compound-immobilized carrier, into contact with each other may be performed by applying the group of isotope-labeled proteins to the column. In the case where the compound-immobilized carrier is put to an appropriate tube, the above-mentioned step may be performed by adding the group of isotope-labeled proteins to the tube.

Then, it is desirable to wash the compound-immobilized carrier with an appropriate solution. In the case where an appropriate column is filled with the compound-immobilized carrier, the washing operation may be performed by adding an appropriate solution to the column. In the case where the compound-immobilized carrier is put to an appropriate tube, the washing operation may be performed by adding an appropriate solution to the tube and conducting a centrifugal operation.

Then, the group of isotope-labeled proteins are eluted with an appropriate solution. The elution solution is not specifically limited. A usable elution solution is, for example, 6 M guanidine hydrochloride, 8 M urea, 2% CHAPS, or about 10 mM ATP or GTP. In the case where an appropriate column is filled with the compound-immobilized carrier, the step of eluting the group of isotope-labeled proteins may be performed by applying an appropriate solution to the column. In the case where the compound-immobilized carrier is put to an appropriate tube, the step of eluting the group of isotope-labeled proteins may be performed by adding an appropriate solution to the tube and conducting a centrifugal operation.

By these methods, a group of proteins bound to the compound immobilized on the carrier can be purified.

The temperature for the above-described operation is not specifically limited, but is preferably 4° C. to 37° C., and more preferably 4° C. to 20° C.

(2)(b) Step of Using a Compound-Immobilized Carrier to Purify Plural Kinds of Proteins Bound to the Compound on the Carrier, from a Group of Proteins Brought into Contact with a Compound Beforehand The group of proteins used in step (b) may be a group of proteins labeled with an isotope different from the isotope in the "group of isotope-labeled proteins" in step (a) as well as a group of non-isotope-labeled proteins. In the following description, a group of non-isotope-labeled proteins will be used. In the case of a group of different-isotope-labeled proteins, the purification may be performed in substantially the same manner.

A group of non-isotope-labeled proteins, and a non-immobilized compound, are brought into contact with each other. Then, the group of non-isotope-labeled proteins which are brought into contact with the non-immobilized compound are purified with a compound-immobilized carrier. By this, from the group of non-isotope-labeled proteins which are brought into contact with the non-immobilized compound, plural kinds of proteins bound to the compound immobilized on the carrier can be purified.

Hereinafter, this will be described in detail.

First, a group of non-isotope-labeled proteins are dissolved in an appropriate solution. Then, the group of non-isotope-labeled proteins, and a non-immobilized compound, are brought into contact with each other.

The compound (non-immobilized compound) to be brought into contact with the group of non-isotope-labeled proteins is not specifically limited. Usable compounds include, for example, synthesized compounds having a low molecular weight, synthesized peptides, purified or partially purified polypeptides, antibodies, cell released substances from bacteria (including bacterial metabolite), intra-biological nucleic acid substances (e.g., ATP, GTP, NAD/NADH, or NADP/NADPH), and lipid. Such a compound may be a novel compound or a known compound. Such a compound has a predefined activity.

The compound (non-immobilized compound) to be brought into contact with the group of non-isotope-labeled proteins may be one type of compound, but preferably a plurality of, for example, five or more kinds of compounds. Such a compound and a compound immobilized on the carrier preferably have a similar structure to each other, with no specific limitation. A non-immobilized compound may contain the compound immobilized to the carrier. A non-immobilized compound and a compound immobilized on the carrier preferably are different in the strength of the predefined activity such as physiological activity or pharmacological activity.

Various conditions for the contact, including the solvent, concentration and incubation of the compound, are not specifically limited and may be set freely. A solution containing a group of non-isotope-labeled proteins dissolved therein include a large amount of proteins and therefore can dissolve even a compound which is poorly water-soluble.

Next, the group of non-isotope-labeled proteins brought into the compound are purified with a compound-immobilized carrier produced in section 1.(1)(a) above. The proteins may be purified by a method substantially the same as "1.(1)(a) Step of using a compound-immobilized carrier to purify plural kinds of proteins bound to the compound on the carrier, from a group of isotope-labeled proteins".

By these methods, from a group of non-isotope-labeled proteins brought into contact with the non-immobilized compound, plural kinds of proteins bound to the compound immobilized on the carrier can be purified.

(3)(c) Step of Mixing the Proteins Obtained in Step (a) and Step (b)

The group of proteins obtained in step (a) and step (b) are mixed at a certain ratio. The certain ratio may or may not be 1:1. In order to improve the dynamic range of the intensity ratio described later, it is preferable to mix an excessive amount (e.g., twice to ten times) of the plural kinds of proteins obtained in "1.(2)(b) Step of using a compound-immobilized carrier to purify plural kinds of proteins bound to the compound on the carrier, from a group of proteins brought into contact with a compound beforehand" to the plural kinds of proteins obtained in "1.(1)(a) Step of using a compound-immobilized carrier to purify plural kinds of proteins bound to the compound on the carrier, from a group of isotope-labeled proteins".

(4)(d) Step of Analyzing the Mixture Obtained in Step (c) with Mass Spectrometry The mixture obtained in step (c) is treated with mass spectrometry. The mixture may be analyzed with mass spectrometry, but is preferably first treated with enrichment (by, for example, Amicon Ultra-15 10,000 MWCO) or separation or digestion described later. A mixture treated with separation or digestion described later will be referred to as "separated proteins" or "digested proteins". A method for separation may be, for example, two-dimensional electrophoresis, SDS-PAGE, or various types of chromatography (e.g., affinity chromatography, reverse phase chromatography, anion exchange chromatography, or cation exchange chromatography). The method is not limited to these, and an appropriate technique may be selected. A method for digestion is, for example, enzymatic digestion or chemical decomposition. Enzymatic digestion is preferable, but the method is not limited to these and an appropriate technique may be selected. An enzyme used for enzymatic digestion is, for example, trypsin, chymotrypsin, Lys-C, Asp-N or Glu-C. Trypsin is preferable. For enzymatic digestion, it is desirable to add a surfactant, preferably, 5-cyclohexyl-pentyl-beta-D-maltoside (U.S. Pat. Nos. 5,674,987 and 5,763,586, Anatrace Inc., Maumee, Ohio, USA).

The enriched proteins, separated proteins or digested proteins thus obtained may be separated with HPLC. The resultant proteins will be referred to as "HPLC separated proteins". For HPLC, an appropriate column may be selected by the technological common sense of those skilled in the art. An anion exchange column or a cation exchange column is preferable. Various conditions for HPLC (flow rate, detector, mobile phase, etc.) may be appropriately selected by the technological common sense of those skilled in the art.

Next, the plural kinds of proteins obtained by the above-described operation are treated with mass spectrometry using a mass spectrometer. As the spectrometer, a general-purpose device is usable, such as a gas chromatography mass spectrometry (GC/MS) device, which is a mass spectrometer combined with a gas chromatography device, or a liquid chromatography mass spectrometry (LC/MS) device, which is a mass spectrometer combined with a liquid chromatography device. An ionization method used by the mass spectrometer may be appropriately selected in accordance with the device to be used. A usable ionization method is, for example, MALDI (matrix-assisted laser desorption/ionization), ESI (electrospray ionization), EI (electron impact ionization), CI (chemical ionization), APCI (atmospheric pressure chemical ionization), FAB (fast atom bombardment), LD, FD, SIMS, or TSP. MALDI or ESI is preferable. An analyzer may be appropriately selected in accordance with the device to be used. For example, a general-purpose device of TOF (time of flight) type, ion trap type, double-focusing type, quadruple pole type, Fourier transformation type or the like is usable. The device and method for mass spectrometry are not limited to those mentioned above, and a device and a method usually used by those skilled in the art for mass spectrometry may be appropriately selected.

(5)(e) Step of Identifying Each of Plural Kinds of Proteins Based on Information Obtained by the Mass Spectrometry Using data obtained as a result of the measurement performed with a mass spectrometer, each of a plurality of proteins may be identified. Namely, the obtained data may be analyzed using software (e.g., SonarMSMS (produced by Genomic Solution) and a database (e.g., NCBInr (http://www.ncbi.nlm.nih.gov/), IPI, or Sport) so as to identify proteins in the sample. It would be easy to those skilled in the art to identify proteins using the measurement data obtained with a mass spectrometer (Nat Genet. 1998: 20, 46-50; J Cell Biol. 1998: 141, 967-977; J Cell Biol. 2000: 148, 635-651; Nature. 2002: 415, 141-147; Nature. 2002: 415, 180-183; Curr Opin Cell Biol. 2003: 15, 199-205; Curr Opin Cell Biol. 2003: 7, 21-27). It would be easy to those skilled in the art to obtain amino acid sequence information from the information on the identified proteins.

(6)(f) Step of Obtaining, Regarding Each Protein, an Intensity Ratio Between a Peak Derived from the Protein Obtained in Step (a) and a Peak Derived from the Protein Obtained in Step (b), Thereby Quantitating an Affinity Ratio of the Compound to Each Protein In the present invention, the expression "peak derived from the protein obtained in step (a)" refers to the signal intensity derived from each of the group of isotope-labeled proteins or a sum thereof (usually represented by area as can be appreciated by those skilled in the art) in the mass spectra obtained from the measurement result of the mass spectrometry (hereinafter, such a peak will occasionally be referred to simply as the "labeled peak").

In the present invention, the expression "peak derived from the protein obtained in step (b)" refers to the signal intensity derived from each of the group of non-isotope-labeled proteins or the group of different-isotope-labeled proteins, or a sum thereof, in the mass spectra obtained from the measurement result of the mass spectrometry (hereinafter, such a peak will occasionally be referred to simply as the "non-labeled peak").

Using the data obtained as a result of the measurement performed with mass spectrometry, the intensity ratio between the non-labeled peak and the labeled peak (="intensity of the non-labeled peak"/"intensity of the labeled peak") (hereinafter, occasionally referred to simply as the "peak intensity ratio") is obtained for each protein. Thus, the affinity ratio of the compound to each protein can be quantitated.

The isotope-labeled proteins have a larger molecular weight than the non-isotope-labeled proteins by a difference corresponding to the isotope-labeled molecules, and thus are observed as a pair of peaks in the mass spectra. The molecular weight of the isotope-labeled proteins may be calculated from the identified proteins and the amino acid sequences thereof.

From the group of proteins used in step (b), proteins bound to the non-immobilized compound are less likely to be bound to the compound on the carrier due to the binding thereof to the non-immobilized compound. Therefore, the non-labeled peak of such proteins is small in the mass spectra. The peak intensity ratio is smaller than the ratio used in step (c) for mixing the proteins obtained in step (b) and the proteins obtained in step (a) (=the mixed amount of the proteins obtained in step (b)/the mixed amount of the proteins obtained in step (a)) (hereinafter, occasionally referred to as the "protein mixing ratio"). By contrast, the proteins which are not bound to the non-immobilized compound is not influenced by the binding thereof to the compound-immobilized carrier. Therefore, the non-labeled peak of such proteins does not become small. Thus, there is no difference between the peak intensity ratio and the protein mixing ratio. In a comparison among non-immobilized compounds having different predefined activities such as physiological activity, biological activity, pharmacological activity and binding activity, the non-labeled peak of a certain protein may be smaller about the same amount with respect to the non-immobilized compounds, i.e., the peak intensity ratio of a certain protein may be smaller about the same amount with respect to the non-immobilized compounds. Such a protein is considered not to be a specific binding protein which is important to the activity of the compounds having an activity, i.e., the non-immobilized compounds used for the comparison.

Even when a non-immobilized compound having a predefined activity (referred to as "compound C" for the sake of explanation) has a low concentration, the mass spectra may exhibit that the non-labeled peak of a certain protein is smaller, i.e., the peak intensity ratio is smaller than the protein mixing ratio. Such a protein may possibly be important to the activity of the non-immobilized compound. Similarly, when the non-labeled peak of a certain protein is not influenced and does not become smaller in mass spectra, i.e., the peak intensity ratio of a certain protein is not influenced, by another non-immobilized compound having a similar structure to, but a different predefined activity such as physiological activity, biological activity, pharmacological activity or binding activity from compound C, there is a high possibility that such a protein is a specific binding protein which is important to the predefined activity of compound C.

When the affinity between a non-immobilized compound and a protein is very weak (it is not known how weak) and the concentration of the non-immobilized compound is low, the non-immobilized compound bound to the protein may possibly be replaced with a compound immobilized to the column at a high concentration while the compound passes through the column. Such an influence may be lowered by increasing the concentration of the non-immobilized compound.

By these methods, a structural affinity relationship between plural kinds of proteins and at least one type of compound can be analyzed at the same time, simply and efficiently.

Figure 2:
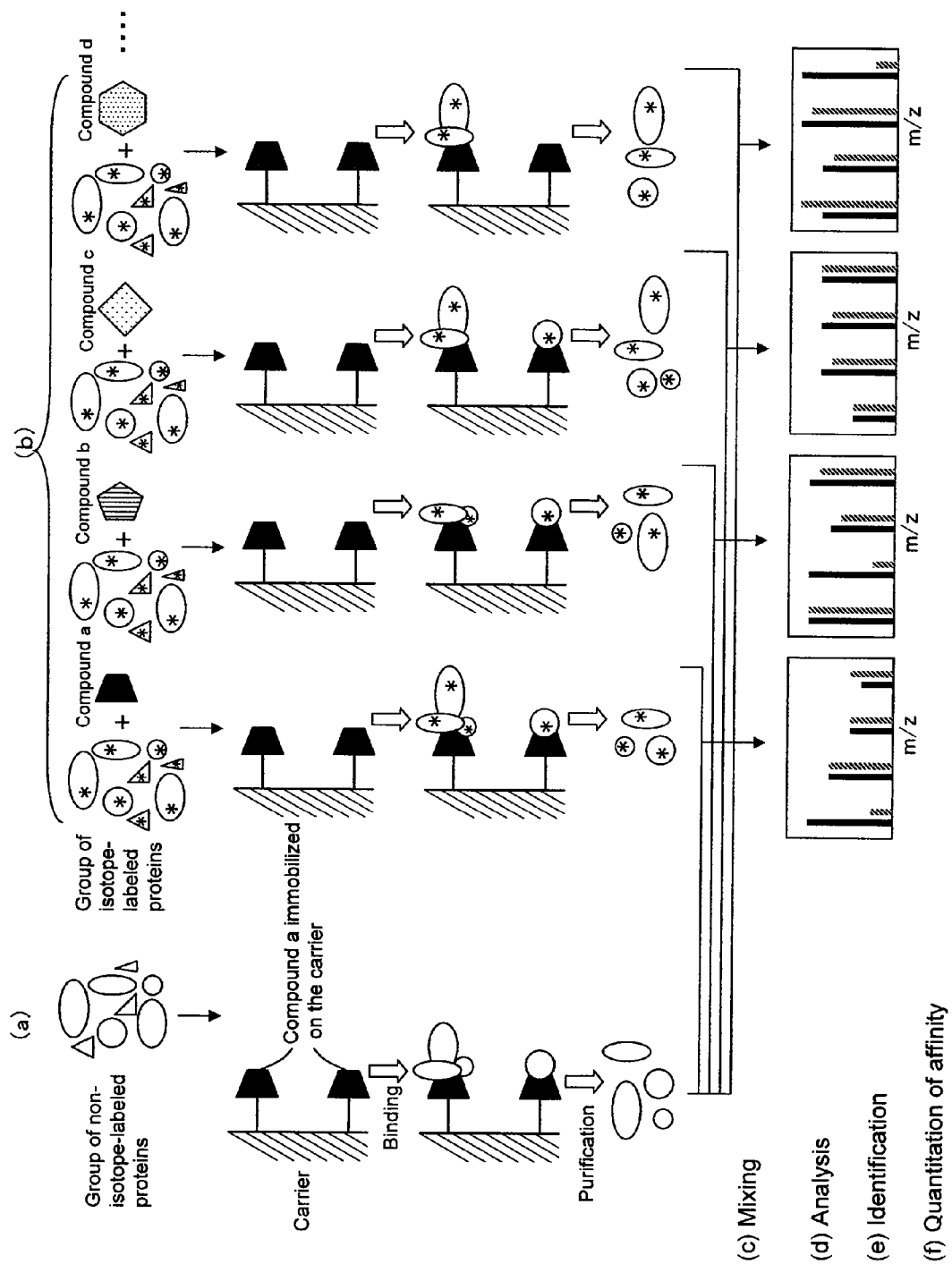
FIG. 2 schematically shows the first embodiment of the present invention.

In the above description of the analyzing method, the group of isotope-labeled proteins are not brought into contact with the compound, but the group of non-isotope-labeled proteins are brought into contact with the compound (see FIG. 1). Those skilled in the art would easily understand that the analyzing method according to the present invention can be carried out in the state where the group of non-isotope-labeled proteins are not brought into contact with the compound, but the group of isotope-labeled proteins are brought into contact with the compound (see FIG. 2). In this case, the peak intensity ratio is obtained by "the labeled peak intensity"/"the non-labeled intensity". Instead of the group of non-isotope-labeled proteins, a group of different-isotope-labeled proteins may be used to carry out the analyzing method according to the present invention.

By examining the affinity with various compounds in a similar manner using a compound-immobilized carrier (e.g., a carrier or column having ATP, GTP, NAD/NADH, NADP/NADPH or the like immobilized thereon), a structural affinity relationship between a compound binding to an ATP, GTP, NAD/NADH, or NADP/NADPH binding site of a specific protein and such a protein can be found.

This method uses an isotope. Therefore, quantitative information can be obtained by calculating the peak intensity ratio in the mass spectra, in addition to based on the presence/absence of the band on the SDS-PAGE. Such information is important to researchers in the field of compound synthesis. Conventionally, a structural affinity relationship is analyzed by examining an activity value of a compound with respect to one target molecule or one assay system while varying the compound. In this manner, it was determined what compounds should be synthesize next. With the method according to the present invention, a structural affinity relationship between one or plural kinds of compounds and plural kinds of proteins can be comprehensively analyzed. Namely, from the viewpoint of one compound, the difference in specificity with respect to the plural kinds of proteins bindable to the compound can be quantitatively evaluated. From the viewpoint of one protein, the difference in binding with respect to the plural kinds of compounds can be quantitatively checked.

The present invention also provides a system for analyzing a structural affinity relationship between plural kinds of proteins and a compound, comprising:

(a) means for using a compound-immobilized carrier to purify plural kinds of proteins bound to the compound on the carrier, from a group of isotope-labeled proteins;

(b) means for using a compound-immobilized carrier to purify plural kinds of proteins bound to the compound on the carrier, from a group of proteins brought into contact with a compound beforehand;

(c) means for mixing the proteins obtained by means (a) and means (b);

(d) means for analyzing the mixture obtained by means (c) with mass spectrometry;

(e) means for identifying each of plural kinds of proteins based on information obtained by the mass spectrometry;

(f) means for obtaining, regarding each protein, an intensity ratio between a peak derived from the protein obtained by means (a) and a peak derived from the protein obtained by means (b), thereby quantitating an affinity ratio of the compound to each protein.

(a) Means for using a compound-immobilized carrier to purify plural kinds of proteins bound to the compound on the carrier, from a group of isotope-labeled proteins, is the same as means used for "1.(1)(a) step of using a compound-immobilized carrier to purify plural kinds of proteins bound to the compound on the carrier, from a group of isotope-labeled proteins".

(b) Means for using a compound-immobilized carrier to purify plural kinds of proteins bound to the compound on the carrier, from a group of proteins brought into contact with a compound beforehand, is the same as means used for "1.(2)(b) step of using a compound-immobilized carrier to purify plural kinds of proteins bound to the compound on the carrier, from a group of proteins brought into contact with a compound beforehand". The proteins used by means (b) may be a group of non-isotope-labeled proteins or a group of isotope-labeled proteins labeled with an isotope different from the isotope used by means (a).

(c) Means for mixing the proteins obtained by means (a) and means (b) is the same as means used for "1.(3)(c) step of mixing the proteins obtained in step (a) and step (b)".

(d) Means for analyzing the mixture obtained by means (c) with mass spectrometry is the same as means used for "1.(4)(d) step of analyzing the mixture obtained in step (c) with mass spectrometry".

(e) Means for identifying each of plural kinds of proteins based on information obtained by the mass spectrometry is the same as means used for "1.(5)(e) step of identifying each of plural kinds of proteins based on information obtained by the mass spectrometry".

(f) Means for obtaining, regarding each protein, an intensity ratio between a peak derived from the protein obtained by means (a) and a peak derived from the protein obtained by means (b), thereby quantitating an affinity ratio of the compound to each protein, is the same as means used for "1.(6)(f) step of obtaining, regarding each protein, an intensity ratio between a peak derived from the protein obtained in step (a) and a peak derived from the protein obtained in step (b), thereby quantitating an affinity ratio of the compound to each protein".

In the above description of the analyzing system, the group of isotope-labeled proteins are not brought into contact with the compound, but the group of non-isotope-labeled proteins are brought into contact with the compound, before purification (first embodiment, FIG. 1). Those skilled in the art would easily understand that the analyzing system according to the present invention can also be realized in an embodiment where the group of non-isotope-labeled proteins are not brought into contact with the compound, but the group of isotope-labeled proteins are brought into contact with the compound, before purification (FIG. 2), simply by replacing elements in the system as necessary. In this case, the peak intensity ratio is obtained by "the labeled peak intensity"/"the non-labeled intensity". Instead of the group of non-isotope-labeled proteins, a group of different-isotope-labeled proteins may be used to realize the analyzing system according to the present invention.

Hereinafter, a system for analyzing a structural affinity relationship between plural kinds of proteins and a compound in the first embodiment of the present invention will be described in detail. In the following exemplary description, the group of proteins used by means (b) is non-isotope-labeled proteins.

Figure 6:
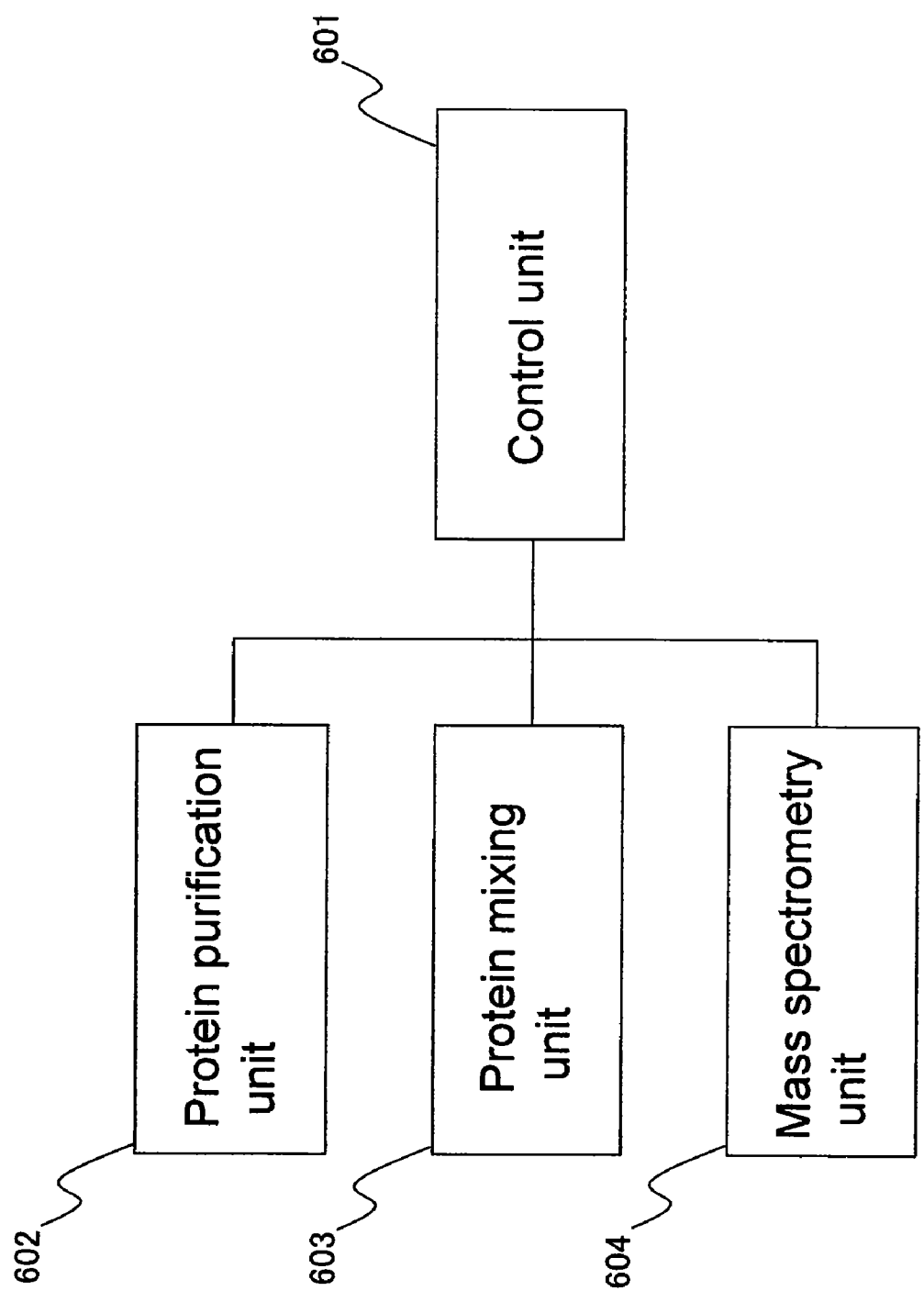
FIG. 6 is a block diagram showing a structure of a system according to the present invention.

FIG. 6 is a block diagram showing a structure of a system according to the present invention. As shown in FIG. 1, the system according to the present invention includes a control unit 601, a protein purification unit 602, a protein mixing unit 603, and a mass spectrometry unit 604.

The control unit 601 controls the entire operation of each unit necessary for carrying out the method according to the present invention. The protein purification unit 602, the protein mixing unit 603 and the mass spectrometry unit 604 are each connected to the control unit 601, and are each controlled by the control unit 601 so as to operate independently or in association with one another. For example, for carrying out the method according to the present invention mainly in a batch system, the units (the protein purification unit 602, the protein mixing unit 603 and the mass spectrometry unit 604) are each controlled independently by the control unit 601, and the control unit 601 instructs each unit to perform a respective operation. For carrying out the method according to the present invention mainly in a flow system, the control unit 601 monitors the operation of each unit, for example, how each unit proceeds with the operation, and the units are controlled in association with one another.

The protein purification unit 602 is a unit for purifying proteins, and includes a cell culture device, a cell crushing device, a compound contact device, a carrier for performing chromatography or the like, a recollection device for the purified proteins and the like. The elements included in the purification unit are controlled independently or in association with one another by an instruction from the control unit 601.

The protein mixing unit 603 is a unit for mixing the proteins purified by the protein purification unit 602. The protein mixing unit 603 is connected to the control unit 601, and performs mixing upon receiving an instruction on the mixing amount, the mixing ratio and the like from the control unit 601.

The mass spectrometry unit 604 is a unit for analyzing the mixed proteins to mass spectrometry, and includes a spotter for spotting the mixed proteins on a measurement plate, a tray for putting the measurement plate on the mass spectrometer and the like. The elements in the mass spectrometry unit 604 are connected to the control unit 601, and executes mass spectrometry in accordance with an instruction from the control unit 601.

Figure 7:
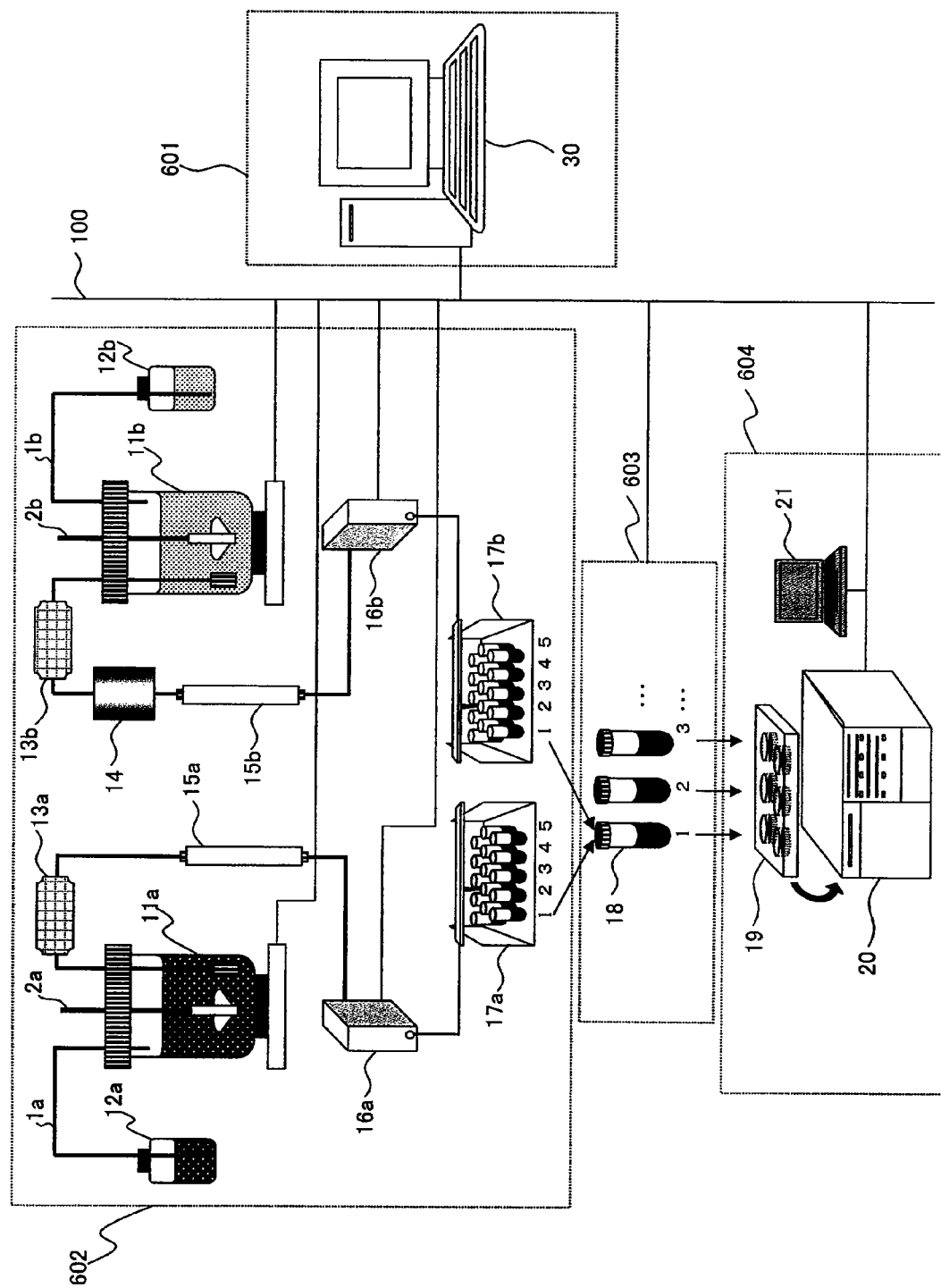
FIG. 7 is a schematic view of each unit of the system according to the present invention.

FIG. 7 is a schematic view showing an embodiment of the units.

As shown in FIG. 7, the protein purification unit 602 includes culture devices 11a and 11b, culture liquid bottles 12a and 12b, cell crushing devices 13a and 13b, a compound contact device 14, compound-immobilized carriers 15a and 15b, protein purification control devices 16a and 16b, and purified protein separators 17a and 17b.

The culture devices 11a and 11b are devices for culturing cells, and culture cells for a predefined time period while adjusting the temperature, $CO_2$ concentration and the like. The culture devices 11a and 11b are respectively connected to the culture liquid bottles 12a and 12b. The culture liquid bottles 12a and 12b may supply a culture liquid to the culture devices via tubes 1a and 1b, respectively. The culture devices 11a and 11b may respectively include stirring blades 2a and 2b. The culture devices 11a and 11b are shown here as vessels for culturing floating cells, but this is merely one embodiment for illustrating the system according to the present invention. The present invention is not limited to this. For culturing cells adhering to the culture plates, those skilled in the art could select culture devices in accordance with the purpose. The culture devices 11a and 11b are connected to the control unit 601 via a LAN 100.

The culture liquid bottles 12a and 12b are vessels for storing a culture liquid for culturing cells. In the first embodiment of the present invention, the culture liquid bottle 12a contains amino acids for isotope-labeling proteins and the like in a mixed state. The culture liquid bottles 12a and 12b may be connected to the control unit 601 via the LAN 100.

The cell crushing devices 13a and 13b are devices for crushing cultured cells to obtain proteins. The cell crushing devices 13a and 13b perform the step of collecting the cells from the culture devices 11a and 11b and crushing the cells, thereby obtaining a suspension of a group of proteins. The cell crushing devices 13a and 13b may be connected to the control unit 601 via the LAN 100.

The compound contact device 14 is a device for bringing proteins and a compound into contact with each other. In the embodiment shown in FIG. 7 (first embodiment of the present invention), the compound contact device 14 is located next to the cell crushing device 13b in order to bring a group of non-isotope-labeled proteins and a compound into contact with each other before application to the carrier. As another aspect of the first embodiment, the compound contact device 14 may be located next to the cell crushing device 13a in order to bring a group of isotope-labeled proteins and a compound into contact with each other before application to the carrier, as would be easily understood by those skilled in the art. The compound contact device 14 may be connected to the control unit 601 via the LAN 100.

The compound-immobilized carriers 15a and 15b are columns for purifying proteins, and have a compound immobilized inside.

For analyzing a structural affinity relationship between plural kinds of proteins and plural kinds of compounds, the group of proteins may be brought into contact with each compound by the compound contact device 14. In this case, before the proteins are brought into contact with each compound by the compound contact device 14, all the samples derived from the culture cell 11b are the same as a result of being treated in the same manner. Therefore, the group of proteins to be introduced into the compound contact device 14 may be sampled using a different culture device 11b and a different cell crushing device 13b for each compound. Alternatively, one culture device 11b and one cell crushing device 13b may be used, and the group of proteins sampled therefrom may be divided into a plurality of sets (e.g., the number of sets corresponding to the number of the non-immobilized compounds) and introduced into the compound contact device 14.

In accordance with an instruction from the control unit 601, the protein purification control devices 16a and 16b perform the step of introducing the proteins into the compound-immobilized carriers 15a and 15b, and also sending the carriers therethrough to the purified protein separators 17a and 17b. The protein purification control devices 16a and 16b may be connected to the control unit 601 via the LAN 100.

The purified protein separators 17a and 17b temporarily store the purified proteins obtained in one purification step and the purified proteins obtained in the other purification step. When the amount of the proteins is large, the same type of proteins (proteins purified from the same cell) may be divided into a plurality of bottles.

FIG. 7 shows one type of culture and purification process. Alternatively, a plurality of systems may be provided in parallel so as to allow plural types of culture and purification processes to be performed. In this way, proteins derived from a plurality of different types of cells can be purified. In that case, proteins from different cells need to be stored in different separators. According to the present invention, the purified protein separators 17a and 17b may store different kinds of proteins respectively, or different bottles in each purified protein separator may store different kinds of proteins.

In the embodiment shown in FIG. 7, the purified protein separators 17a and 17b are controlled by the protein purification control devices 16a and 16b, but the present invention is not limited to this. The purified protein separators 17a and 17b may be connected independently to the control unit 601 via the LAN 100.

In FIG. 7, the protein mixing unit 603 is a unit for mixing two different kinds of proteins purified by the protein purification unit 602. In accordance with an instruction from the control unit 601, the protein mixing unit 603 selects samples arranged in the purified protein separators 17a and 17b and mixes the proteins at a certain ratio. In the embodiment shown in FIG. 7, the same numbered sampled are mixed in each tube 18; for example, No. 1 samples are mixed together, and No. 2 samples are mixed together.

The mass spectrometry unit 604 is a unit for analyzing one or plural kinds of proteins as a target of mass spectrometry. In accordance with an instruction from the control unit 601, the mass spectrometry unit 604 spots a sample mixed by the protein mixing unit 603 on a plate 19 for mass spectrometry and executes mass spectrometry using a mass spectrometer 20. For transferring the plate 19 to the mass spectrometer 20, a computer-controlled robot-type sample handling device is also usable.

Mass spectrometry is executed in accordance with an instruction from the control unit 601 via the LAN 100. The mass spectrometry may be executed by a computer 21 provided as an accessory to the mass spectrometer 20.

Mass spectrometry information is transmitted to the control unit 601 via the LAN 100, and is processed to obtain an identification profile, an intensity ratio profile, and an affinity ratio profile of proteins.

The control unit 601 is a central control unit for operating the system according to the present invention, and includes a central computer 30, an internet communication line and the like.

The control unit 601 identifies the proteins, determines the intensity ratio between the isotope-labeled peak and the non-isotope-labeled peak, and the affinity ratio, and displays the results in a display device in the control unit 601. Each piece of data is automatically organized by the control unit 601.

Figure 8:
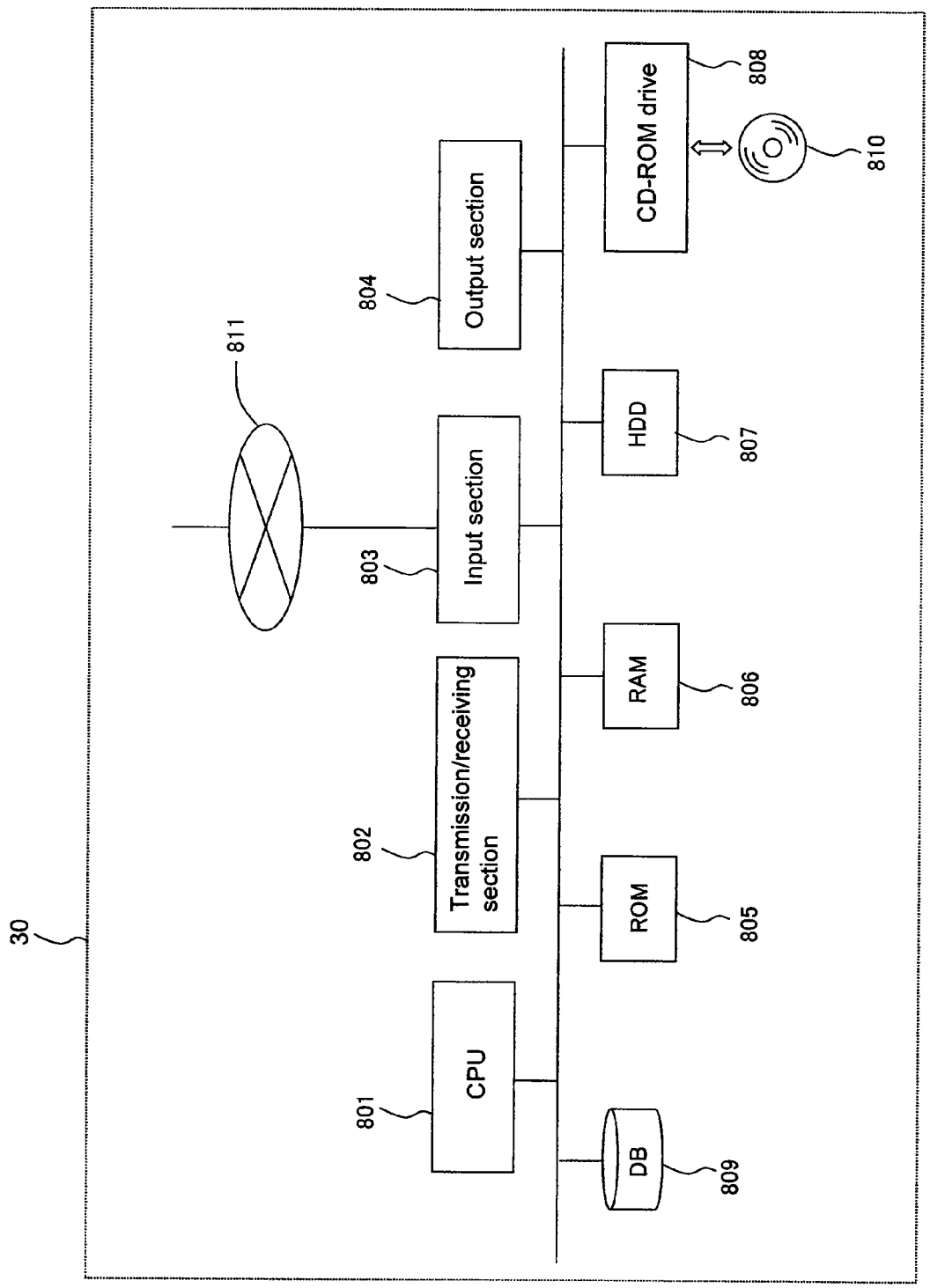
FIG. 8 is a detailed structural view of a control unit.

FIG. 8 is a detailed structural view of the control unit 601. As shown in FIG. 8, the central computer 30 includes a CPU 801, a transmission/receiving section 802, an input section 803, an output section 804, a ROM 805, a RAM 806, a hard disc drive (HDD) 807, a CD-ROM drive 808, and a protein database (hereinafter, referred to as "DB") 809.

The CPU 801 controls the entire operation of the system according to the present invention, and records data on the mass spectrometry results, data on the identified protein, intensity ratio data, affinity data and the like on the DB 809. The CPU 801 may control the communication of the transmission/receiving section 802 and use the data stored on the DB 809 to check data of other proteins via the Internet 811.

In accordance with an instruction from the CPU 801, the transmission/receiving section 802 performs data transmission and receiving between the protein purification unit 602, the protein mixing unit 603, and the mass spectrometry unit 604.

The input section 803 is a keyboard, a mouse, a touch panel or the like, and is operated when the user inputs information or updates the database. The output section 804 is an LCD (liquid crystal display) or the like. For updating various databases, the output section 804 converts the code data from the CPU 801 into display data each time the code data is received, and displays the data. The ROM 805 stores a processing program of the system according to the present invention. The RAM 806 temporarily stores data necessary for processing executed by the system according to the present invention. The HDD 807 is a drive for storing mass spectrometry data and the like. In accordance with an instruction from the CPU 801, the CD-ROM drive 808 reads a program or the like necessary for executing the processing by the system according to the present invention (for executing the processing in various embodiments), which is stored on a CD-ROM 810, and writes the program onto the RAM 806 or the like. Instead of the CD-ROM, a rewritable medium such as a CD-R, CD-RW or the like may be used as a storage medium. In that case, a drive for CD-R or CD-RW is provided instead of the CD-ROM drive 808. Instead of the above-mentioned mediums, a DVD, MO, flash memory stick or the like may be used and a corresponding drive may be provided.

The central computer 30 communicates with the protein purification unit 602, the protein mixing unit 603, and the mass spectrometry unit 604, and transmits control information such that these units function. The central computer 30 also receives the protein identification results and the protein mass spectrometry results, and displays the identification results, the intensity ratio and the affinity ratio.

Figure 9:
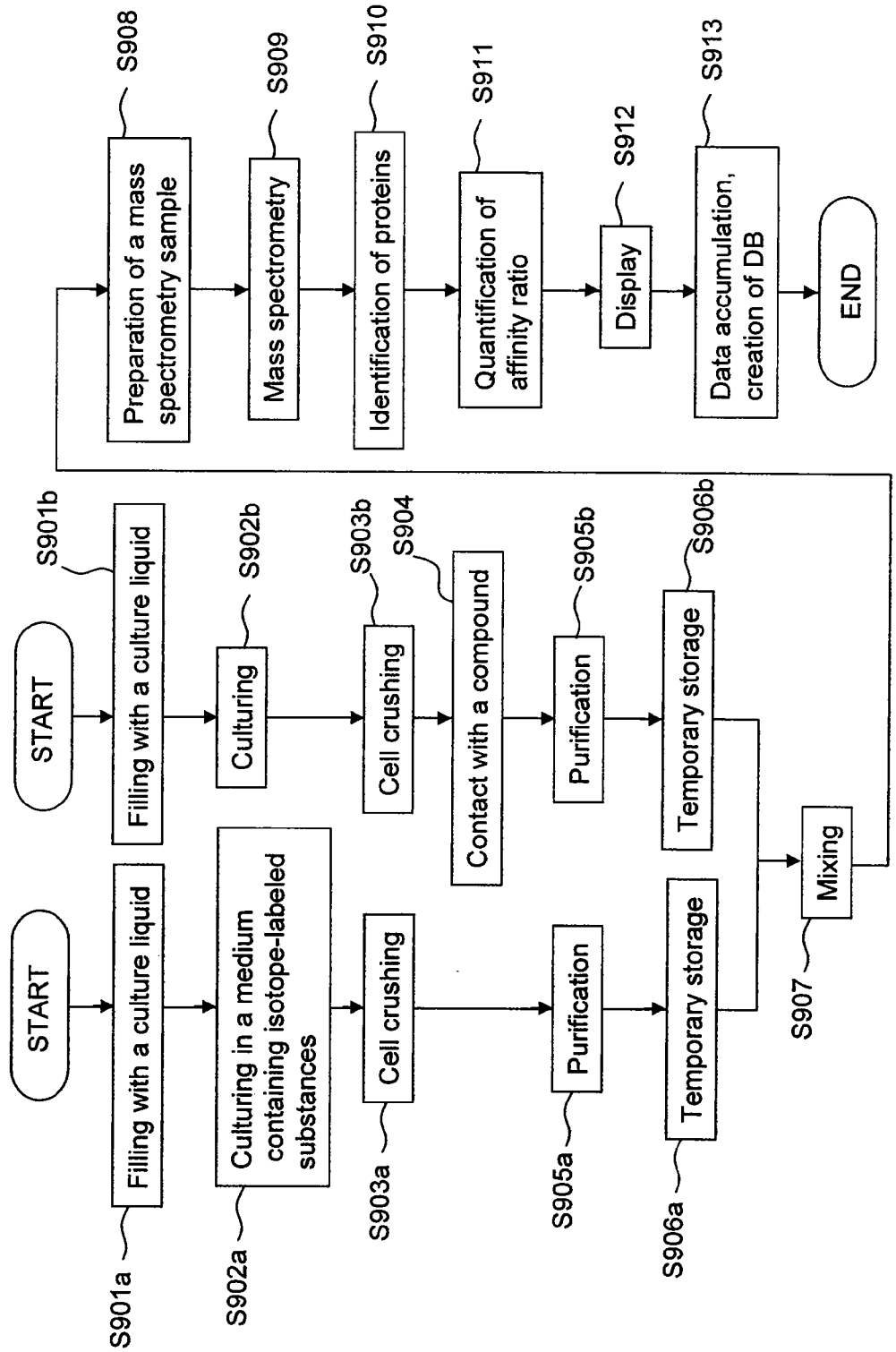
FIG. 9 is a flowchart of an operation of the control unit.

Hereinafter, an operation of the control unit (first embodiment) will be described with reference to the drawing (FIG. 9).

The central computer 30 of the control unit 601 instructs a filling device (not shown) to fill one culture device 11*a* with a culture liquid, a sample (cell) and other reagents necessary to carry out the present invention, and also instructs a sample filling device (not shown) to add an isotope-labeled substance (isotope-labeled amino acid, etc.) necessary for labeling proteins. The filling device performs the filling operation (S901*a*). In parallel, the central computer 30 instructs the sample filling device (not shown) to fill the other culture device 11*b* with a culture liquid, a sample (cell) and other reagents necessary to carry out the present invention. The sample filling device performs the filling operation (S901*b*). When each of the culture devices 11*a* and 11*b* are filled with the culture liquid and the like, the central computer 30 instructs each culture device 11*a*, 11*b* to culture under a predefined condition. Each culture device 11*a*, 11*b* performs the culture operation (S902*a*, S902*b*). The "predefined condition" may be regarding the culturing time, the culturing temperature, the $CO_2$ concentration, whether or not to stir, or the like. When the culture operation under the predetermined condition is completed, the central computer 30 instructs the cell crushing devices 13*a* and 13*b* to perform the cell crushing step. The cell crushing devices 13*a* and 13*b* performs the cell crushing operation (S903*a*, S903*b*). After the cell sampled from the medium containing the isotope-labeled substance is crushed in S903*a*, the central computer 30 instructs the carrier 15*a* having a predetermined compound immobilized thereon to perform the protein purification step. The carrier purifies the proteins (S905*a*). After the cell sampled from the medium not containing the isotope-labeled substance is crushed in S903*b*, the central computer 30 instructs the compound contact device 14 to bring the crushed substance (group of proteins) into contact with the compound. The compound contact device 14 performs the contact operation (S904). After the proteins are brought into contact with the compound, the proteins are purified as in S905*a* (S905*b*). When the purification of the proteins is completed, the central computer 30 instructs the protein purification control devices 16*a* and 16*b* to separate the protein samples into the purified protein separators 17*a* and 17*b* and temporarily store the protein samples in preparation of the subsequent mixing (S907). The protein purification control devices perform the separation and temporary storage operation (S906*a*, S906*b*). Then, the central computer 30 instructs the protein mixing unit 603 to mix the separated purified proteins. The protein mixing unit 603 mixes the purified proteins (S907).

When the mixing is completed, the central computer 30 instructs to prepare a sample for mass spectrometry (S908). The mass spectrometry sample preparation step may be performed in a well tray for culture or a different well tray (S908). Next, the central computer 30 instructs the spotter (not shown) to spot the prepared sample to a mass spectrometry plate (e.g., the plate 19 in FIG. 7) and then start the mass spectrometry of the sample. The spotter performs the spotting operation, and the mass spectrometer starts the mass spectrometry (S909).

The central computer 30 identifies the proteins (S910), and finds the intensity ratio between the labeled peak and the non-labeled peak of each protein and quantitates the affinity ratio of the compound to each protein (S911). The data on the protein identification results and the intensity ratio are transmitted to the central computer 30, and a display of the output device or the computer displays the identification results and the affinity ratio (S912).

The central computer 30 checks the data on the intensity ratio and the identification results with respect to the existing information, and accumulates the data on the hard disc for creating a database (S913).

2. Second Embodiment of the Present Invention

A second embodiment of the present invention provides a method for analyzing a structural affinity relationship between plural kinds of proteins and a compound, comprising the steps of:

(a) using a compound-immobilized carrier to purify plural kinds of proteins bound to the compound on the carrier, from a group of proteins;

(b) using a compound-immobilized carrier to purify plural kinds of proteins bound to the compound on the carrier, from a group of proteins brought into contact with a compound beforehand;

(c) isotope-labeling one of the proteins obtained in step (a) and the proteins obtained in step (b);

(d) mixing the labeled proteins obtained in step (c) with the proteins obtained in step (a) or the proteins obtained in step (b) which are not labeled in step (c);

(e) analyzing the mixture obtained in step (d) with mass spectrometry;

(f) identifying each of plural kinds of proteins based on information obtained by the mass spectrometry;

(g) obtaining, regarding each protein, an intensity ratio between a peak derived from the proteins obtained in step (a) and a peak derived from the protein obtained in step (b), thereby quantitating an affinity ratio of the compound to each protein.

Figure 3:
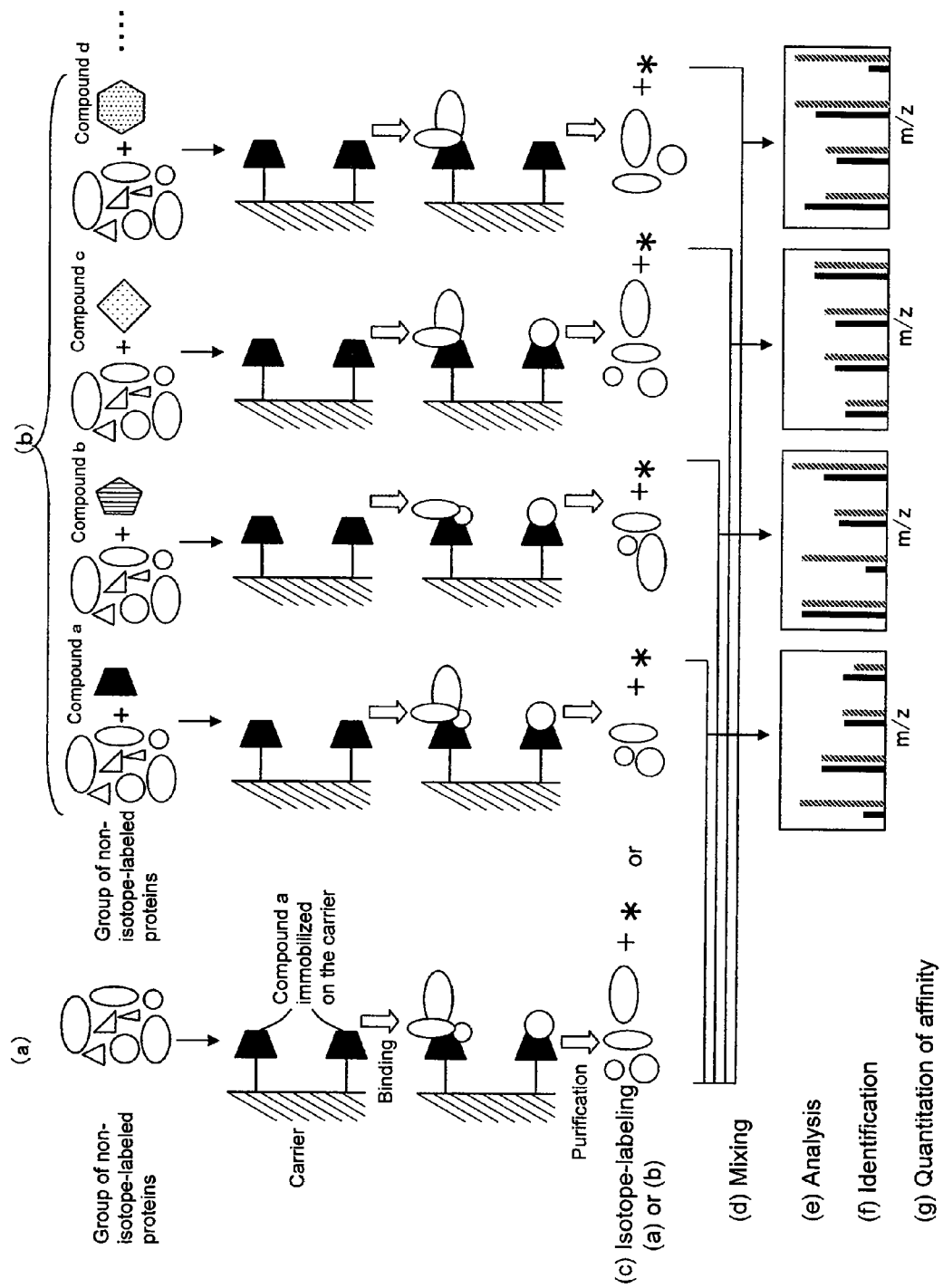
FIG. 3 schematically shows a second embodiment of the present invention.

Hereinafter, the second embodiment of the present invention will be described in detail (see FIG. 3).

(1)(a) Step of Using a Compound-Immobilized Carrier to Purify Plural Kinds of Proteins Bound to the Compound on the Carrier, from a Group of Proteins In this step, plural kinds of proteins bound to the compound immobilized on the carrier can be purified by a method substantially the same as "1.(1)(a) Step of using a compound-immobilized carrier to purify plural kinds of proteins bound to the compound on the carrier, from a group of isotope-labeled proteins".

The proteins used in step (a) may be a group of non-isotope-labeled proteins or a group of isotope-labeled proteins labeled with an isotope different from the isotope used in step (c).

(2)(b) Step of Using a Compound-Immobilized Carrier to Purify Plural Kinds of Proteins Bound to the Compound on the Carrier, from a Group of Proteins Brought into Contact with a Compound Beforehand In this step, plural kinds of proteins bound to the compound immobilized on the carrier can be purified by a method equivalent to "1.(2)(b) Step of using a compound-immobilized carrier to purify plural kinds of proteins bound to the compound on the carrier, from a group of proteins brought into contact with a compound beforehand".

The proteins used in step (b) may be a group of non-isotope-labeled proteins or a group of isotope-labeled proteins labeled with an isotope different from the isotope used in step (c).

(3)(c) Step of Isotope-Labeling One of the Proteins Obtained in Step (a) and the Proteins Obtained in Step (b)

Either the proteins obtained in step (a) or the proteins obtained in step (b) are isotope-labeled. There is no specific limitation on which proteins are to be isotope-labeled. An isotope used in step (c) may be a radioactive isotope, but a stable isotope with no radioactivity is easy to handle and especially preferable. Usable stable isotope include, with no limitation, $^2H$, $^{13}C$, $^{15}N$, $^{17}O$, $^{18}O$, $^{33}P$, $^{34}S$ or a combination thereof. $^2H$, $^{13}C$, $^{15}N$, or $^{18}O$ or a combination thereof is preferable; $^{13}C$, $^{15}N$, or $^{18}O$ or a combination thereof is more preferable; and $^{13}C$ is especially preferable. According to the present invention, any type of isotope which can label a protein is usable with no specific limitation.

Hereinafter, a practical method for isotope labeling will be described.

A group of proteins obtained by step (a) or step (b) may be isotope-labeled in vitro. For example, the proteins may be isotope-labeled by alkylating cysteine residue in the proteins using an isotope-labeled alkylating reagent (see Rapid Communications in Mass Spectroscopy, Vol. 16, No. 15 (2002), pp. 1416-1424). Alternatively, the proteins may be isotope-labeled by biotinylating cysteine residue in the proteins using an isotope-labeled biotinylating reagent. Using an adipin column, only the labeled proteins may be purified (Nature Biotechnology, Vol. 17, No. 10, October 1999, pp. 994-999).

In addition, C-terminus or N-terminus of peptide fragment, glutamic acid residue, asparaginic acid residue or the like obtained by digesting proteins may be labeled with isotope-labeled molecules. Practically, when digesting proteins with an enzyme, water labeled with $^{18}O$ is added to a buffer solution. An enzyme used for enzymatic digestion is, for example, chymotrypsin, trypsin, Asp-N, Lys-C, or Glu-C. It is known that when chymotrypsin or Asp-N is used, there is one $^{18}O$ at the C-terminus of the post-hydrolysis peptide, and that when trypsin, Lys-C, or Glu-C is used, both of two oxygen atoms of the carboxylic acid at the C-terminus of the post-hydrolysis peptide become $^{18}O$.

Furthermore, a method of methylesterifying the carboxylic acid at the C-terminus of the peptide fragment, glutamic acid residue, or asparaginic acid residue obtained by digesting proteins is known (see Goodlett D R, Keller A, Watts J D, Newitt R, Yi E C, Purvine S, Eng J K, von Haller P, Aebersold, Koller E. Differential stable isotope labeling of peptides for quantitation and de nove sequence derivation. Rapid Commun mass Spectrom. 2001:15, pp. 1214-1221). Isotope labeling may be possible by methylation using isotope-labeled methanol.

A method of forming the N-terminus of the peptide fragment obtained by digesting proteins to a nicotinic acid derivative is known (see Munchbach M, Quadroni M, Miotto G. James P. Quantitation and facilitated de novo sequencing of proteins by isotropic N-terminal labeling of peptides with a fragmentation-directing moiety. Anal. Chem. 2000:72, pp. 4047-4057), and a method of acetylation of N-terminus of the peptide (see Ji. J. Chakraborty A, Geng M, Zhang X, Amini A, Bina M, Regnier F. Strategy for quantitative and quantitative analysis in proteomics based on signature peptides. J Chromatogr B Biomed Sci Appl. 2000:745, pp. 197-210) are known. Thus, isotope labeling is also possible using such isotope-labeled reagents.

(4)(d) Step of Mixing the Labeled Proteins Obtained in Step (c) with the Proteins Obtained in Step (a) or the Proteins Obtained in Step (b) which are not Labeled in Step (c)

This step may be performed by a method equivalent to "1.(3)(c) Step of mixing the proteins obtained in step (a) and step (b)".

(5)(e) Step of Analyzing the Mixture Obtained in Step (d) with Mass Spectrometry This step may be performed by a method substantially the same as "1.(4)(d) Step of analyzing the mixture obtained in step (c) with mass spectrometry".

(6)(f) Step of Identifying Each of Plural Kinds of Proteins Based on Information Obtained by the Mass Spectrometry This step may be performed by a method substantially the same as "1.(5)(e) Step of identifying each of plural kinds of proteins based on information obtained by the mass spectrometry".

(7)(g) Step of Obtaining, Regarding Each Protein, an Intensity Ratio Between a Peak Derived from the Protein Obtained in Step (a) and a Peak Derived from the Protein Obtained in Step (b), Thereby Quantitating an Affinity Ratio of the Compound to Each Protein.

This step may be performed by a method substantially the same as "1.(6)(f) Step of obtaining, regarding each protein, an intensity ratio between a peak derived from the protein obtained in step (a) and a peak derived from the protein obtained in step (b), thereby quantitating an affinity ratio of the compound to each protein". One the proteins obtained in step (a) and the proteins obtained in step (b) are isotope-labeled, and the other are not isotope-labeled. In this case, the peak intensity may be obtained by "the peak intensity derived from the proteins obtained in step (a)"/"the peak intensity derived from the proteins obtained in step (b)".

By these methods, a structural affinity relationship between plural kinds of proteins and at least one type of compound can be analyzed at the same time, simply and efficiently.

The present invention also provides a system for analyzing a structural affinity relationship between plural kinds of proteins and a compound, comprising:

(a) means for using a compound-immobilized carrier to purify plural kinds of proteins bound to the compound on the carrier, from a group of proteins;

(b) means for using a compound-immobilized carrier to purify plural kinds of proteins bound to the compound on the carrier, from a group of proteins brought into contact with a compound beforehand;

(c) means for isotope-labeling one of the proteins obtained by means (a) and the proteins obtained by means (b);

(d) means for mixing the labeled proteins obtained by means (c) with the proteins obtained by means (a) or the proteins obtained by means (b) which are not labeled by means (c);

(e) means for analyzing the mixture obtained by means (d) with mass spectrometry;

(f) means for identifying each of plural kinds of proteins based on information obtained by the mass spectrometry; and (g) means for obtaining, regarding each protein, an intensity ratio between a peak derived from the protein obtained by means (a) and a peak derived from the protein obtained by means (b), thereby quantitating an affinity ratio of the compound to each protein.

(a) Means for using a compound-immobilized carrier to purify plural kinds of proteins bound to the compound on the carrier, from a group of proteins, is equivalent to means used for "1.(1)(a) Step of using a compound-immobilized carrier to purify plural kinds of proteins bound to the compound on the carrier, from a group of isotope-labeled proteins". The proteins used by means (a) may be a group of non-isotope-labeled proteins or a group of isotope-labeled proteins labeled with an isotope different from the isotope used by means (c).

(b) Means for using a compound-immobilized carrier to purify plural kinds of proteins bound to the compound on the carrier, from a group of proteins brought into contact with a compound beforehand, is equivalent to means used for "1.(2) (b) Step of using a compound-immobilized carrier to purify plural kinds of proteins bound to the compound on the carrier, from a group of proteins brought into contact with a compound beforehand". The proteins used by means (b) may be a group of non-isotope-labeled proteins or a group of isotope-labeled proteins labeled with an isotope different from the isotope used by means (c).

(c) Means for isotope-labeling one of the proteins obtained by means (a) and the proteins obtained by means (b) is the same as means used for "2.(3)(c) Step of isotope-labeling one of the proteins obtained in step (a) and the proteins obtained in step (b)".

(d) Means for mixing the labeled proteins obtained by means (c) with the proteins obtained by means (a) or the proteins obtained by means (b) which are not labeled by means (c) is equivalent to means used for "1.(3)(c) Step of mixing the proteins obtained in step (a) and step (b)".

(e) Means for analyzing the mixture obtained by means (d) with mass spectrometry is equivalent to means used for "1.(4)(d) Step of analyzing the mixture obtained in step (c) with mass spectrometry".

(f) Means for identifying each of plural kinds of proteins based on information obtained by the mass spectrometry is equivalent to means used for "1.(5)(e) Step of identifying each of plural kinds of proteins based on information obtained by the mass spectrometry".

(g) Means for obtaining, regarding each protein, an intensity ratio between a peak derived from the protein obtained by means (a) and a peak derived from the protein obtained by means (b), thereby quantitating an affinity ratio of the compound to each protein, is equivalent to means used for "1.(6) (f) Step of obtaining, regarding each protein, an intensity ratio between a peak derived from the protein obtained in step (a) and a peak derived from the protein obtained in step (b), thereby quantitating an affinity ratio of the compound to each protein". In this case, the peak intensity ratio is obtained by "the peak intensity derived from the proteins obtained by means (a)"/"the peak intensity derived from the proteins obtained by means (b)".

A system for analyzing a structural affinity relationship between plural kinds of proteins and a compound in the second embodiment of the present invention is equivalent to the system in the first embodiment described above (FIG. 6, FIG. 7, FIG. 8 and FIG. 9), but the order of the processing and the structure of the protein purification unit 602 are partially different. The protein purification unit 602 may include a protein divider, an isotope labeling control device and the like in addition to the elements described in the first embodiment.

In the second embodiment of the present invention, the isotope labeling means for the proteins is provided at a different location from in the first embodiment, and the isotope-labeled substance is not mixed in the culture liquid bottle 12a in principle. The sample from the culture device 11a is the same as the sample from the culture device 11b before being brought into contact with the compound by the compound contact device 14. Therefore, the group of proteins sampled from one of two different culture devices 11a and 11b may be introduced to the compound contact device 14. Alternatively, only one culture device 11a, 11b or 11c (FIG. 10) may be used. In this case, the group of proteins sampled therefrom may be divided into a plurality of sets (e.g., the number of the non-immobilized compounds+1), and a part thereof may be brought into contact with the compound.

Figure 10:
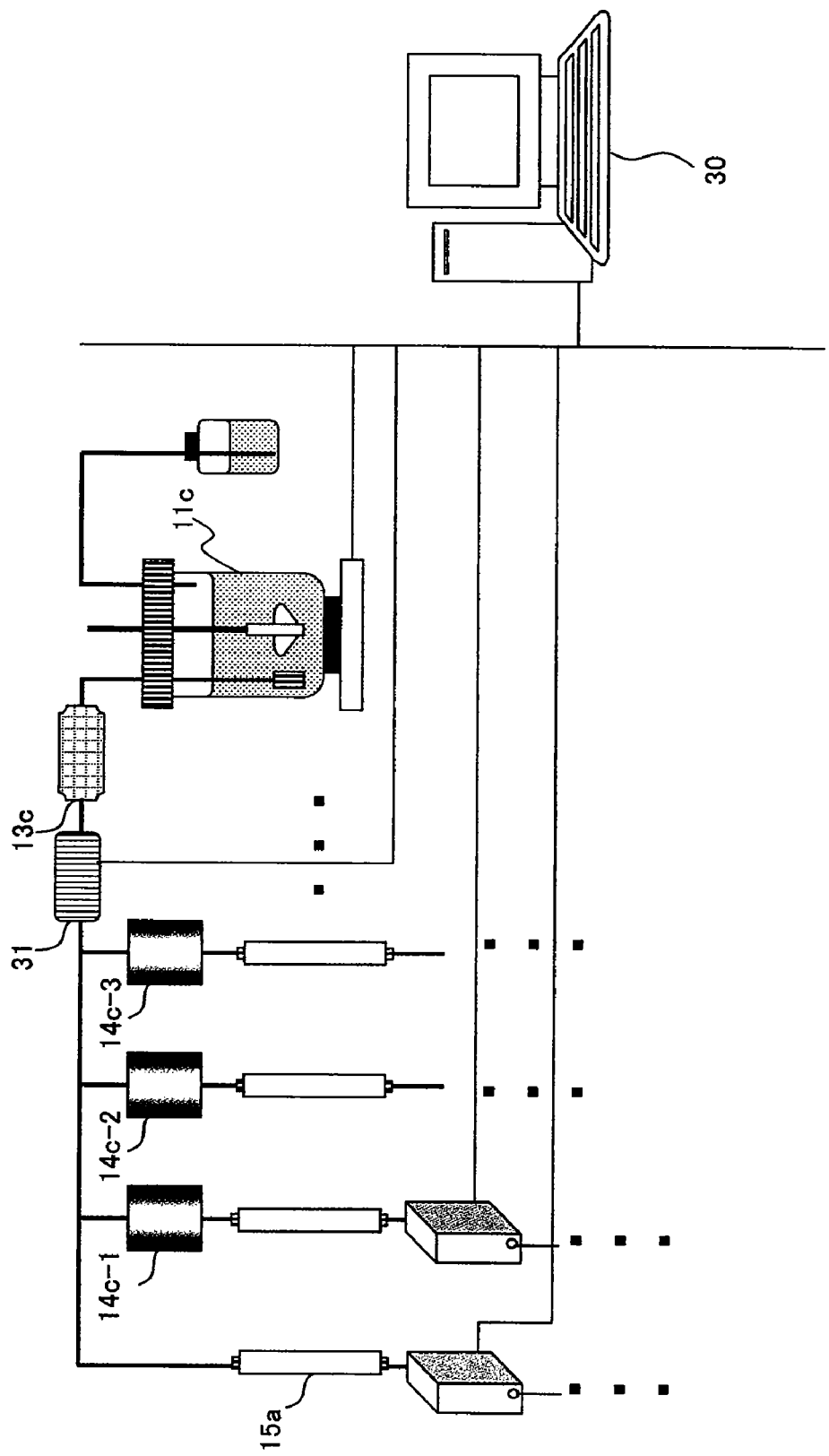
FIG. 10 is a schematic view of a device for dividing a group of proteins sampled from one culture device into a plurality of sets.

FIG. 10 is a schematic view of a device used for dividing a group of proteins sampled from one culture device into a plurality of sets. The group of proteins sampled from one culture device 11c are crushed by a cell crushing device 13c. Then, the central computer 30 instructs a sample divider 31 to divide the post-crushing sample into a plurality of sets, introduce a part thereof to a compound-immobilized carrier 15a and introduce the remaining part to compound contact devices 14c-1, 14c-2 and 14c-3 (FIG. 10 shows three compound contact devices). The sample divider 31 divides the sample into a plurality of sets and introduces the divided samples into the compound-immobilized carrier 15a, and the compound contact devices 14c-1, 14c-2 and 14c-3, respectively.

The step of isotope labeling is performed after the proteins are purified by the compound-immobilized carriers 15a and 15b. After the proteins are purified in S905a and S905b, the central computer 30 instructs the isotope labeling control device (not shown) to isotope-label either the proteins purified in S905a or the proteins purified in S905b. The control device isotope-labels the proteins. The central computer 30 may further instruct the isotope labeling control device to purify the proteins after the labeling. The labeled proteins are separated into the purified protein separators 17a and 17b, and temporarily stored (S906a, S906b).

Alternatively, the step of isotope labeling may be performed after the proteins are separated into the purified protein separators 17a and 17b. After the purified proteins are separated and temporarily stored in S906a and S906b, the central computer 30 instructs the isotope labeling control device (not shown) to isotope-label either the proteins stored in S906a or the proteins stored in S906b. The control device isotope-labels the proteins.

In the second embodiment, the protein mixing unit 603 and the mass spectrometry unit 604 are substantially the same as in the first embodiment.

3. Third Embodiment of the Present Invention

A third embodiment of the present invention provides a method for analyzing a structural affinity relationship between plural kinds of proteins and a compound, comprising the steps of:

(a) using a compound-immobilized carrier to purify plural kinds of proteins bound to the compound on the carrier, from a group of proteins;

(b) mixing the proteins obtained in step (a) and a group of isotope-labeled proteins as an internal standard substance;

(c) analyzing the mixture obtained in step (b) with mass spectrometry;

(d) using a compound-immobilized carrier to purify plural kinds of proteins bound to the compound on the carrier, from a group of proteins brought into contact with a compound beforehand;

(e) mixing the proteins obtained in step (d) and a group of isotope-labeled proteins as an internal standard substance;

(f) analyzing the mixture obtained in step (e) with mass spectrometry;

(g) identifying each of plural kinds of proteins based on information obtained by the mass spectrometry in steps (c) and (f); and (h) obtaining, regarding each protein, an intensity ratio between a peak derived from the protein obtained in step (a) and a peak derived from the protein as an internal standard substance, and an intensity ratio between a peak derived from the protein obtained in step (d) and a peak derived from the protein as an internal standard substance, and comparing the two intensity ratios, thereby quantitating an affinity ratio of the compound to each protein.

Figure 4:
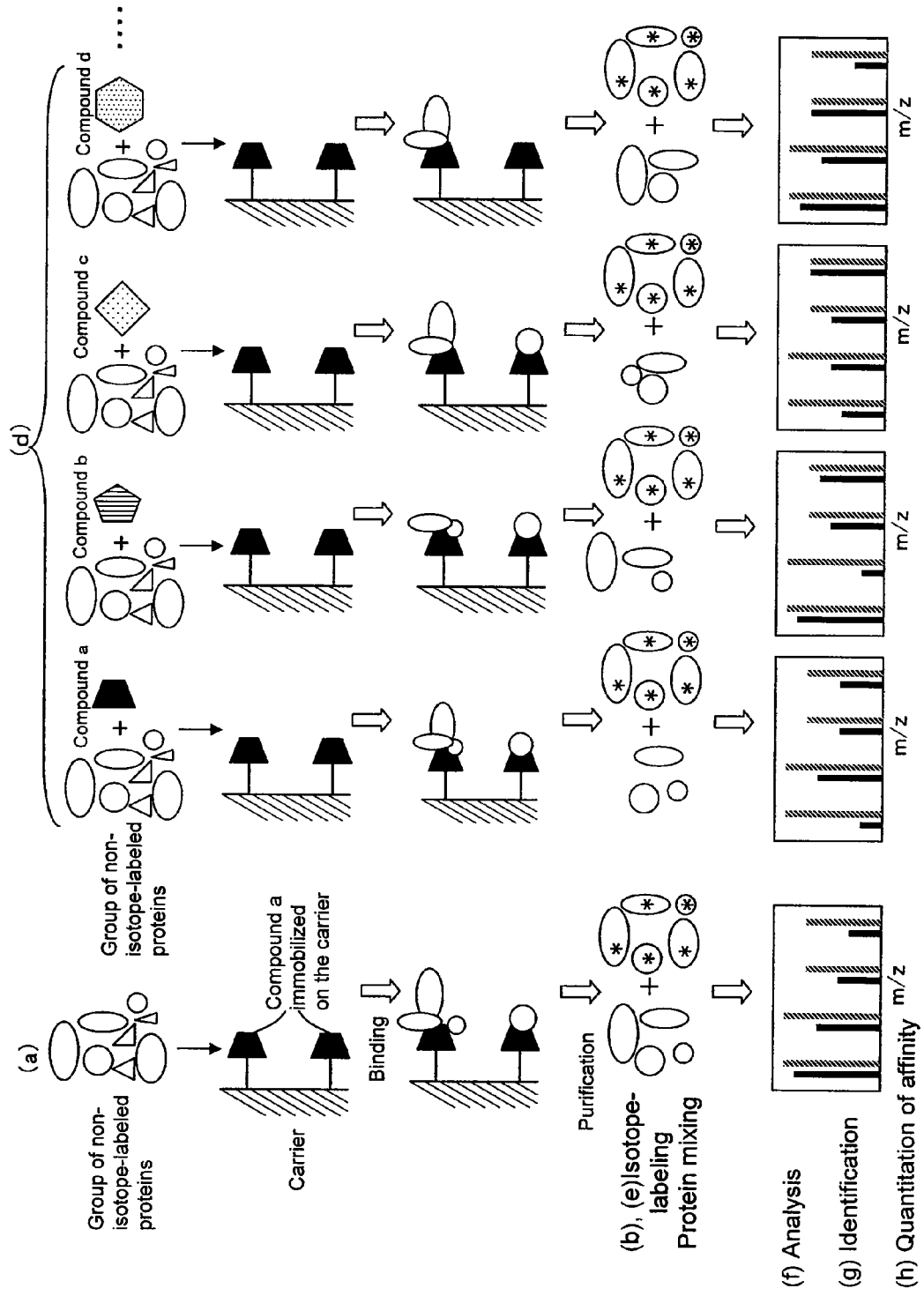
FIG. 4 schematically shows a third embodiment of the present invention.

Hereinafter, the third embodiment will be described in detail (see FIG. 4).

(1)(a) Step of Using a Compound-Immobilized Carrier to Purify Plural Kinds of Proteins Bound to the Compound on the Carrier, from a Group of Proteins In this step, plural kinds of proteins bound to the compound immobilized on the carrier can be purified by a method substantially the same as "1.(1)(a) Step of using a compound-immobilized carrier to purify plural kinds of proteins bound to the compound on the carrier, from a group of isotope-labeled proteins".

The proteins used in step (a) may be a group of non-isotope-labeled proteins. Instead of the group of non-isotope-labeled proteins, a group of isotope-labeled proteins labeled with an isotope different from the isotope used for the internal standard substance in the present invention is also usable.

(2)(b) Step of Mixing the Proteins Obtained in Step (a) and a Group of Isotope-Labeled Proteins as an Internal Standard Substance The proteins obtained in step (a) and a group of isotope-labeled proteins as an internal standard substance are mixed at a certain ratio. The certain ratio may or may not be 1:1. An internal standard substance is a substance acting as a standard in a measurement system. Here, the group of isotope-labeled proteins act as an internal standard substance. The internal standard substance is preferably derived from a biological sample having the same quality as that of the plurality of proteins obtained in step (a), but may be derived from a different biological sample.

Hereinafter, an exemplary method for preparing a group of isotope-labeled proteins which can act as an internal standard substance (hereinafter, occasionally referred to as an "internal standard substance of the present invention") will be described.

An internal standard substance of the present invention may be prepared by metabolic isotope labeling. For example, proteins in a cell may be metabolically isotope-labeled by culturing a culturable cell in a medium containing an isotope-labeled amino acid. Any culturing condition is usable. A medium preferable to culture the cell in a liquid medium or a solid medium may be selected. For example, when an animal cell is selected, a medium such as DMEM, MEM, RPMI1640, IMDM or the like may be used. When necessary, serum such as fetal calf serum (FCS) or the like, amino acid, glucose, penicillin, or streptomycin or the like may be added. Culturing can be performed at a pH of about 6 to 8 and 30 to 40° C. for around 15 to 200 hours. When necessary, the medium may be changed, or ventilation or stirring may be performed.

An internal standard substance of the present invention may be prepared by crushing a cell containing the group of proteins metabolically isotope-labeled thus obtained. A method for crushing may be a method using a Downs-type TEFLON® polytetrafluoroethylene homogenizer, a polytron, a warring blender, a Potter-type glass homogenizer, an ultrasonic crushing device or a cell-dissolved solution (e.g., M-PER: Cat No. 78501, T-PER: Cat No. 78510, both produced by PIERCE), or a freezing and thawing method. A method using a cell-dissolved solution is preferable. The crushed cell is preferably deprived of insoluble substances by centrifugation. In this way, an internal standard substance of the present invention can be prepared.

An isotope used in the present invention may be a radioactive isotope, but a stable isotope with no radioactivity is easy to handle and especially preferable. Usable stable isotope include, with no limitation, $^2H$, $^{13}C$, $^{15}N$, $^{17}O$, $^{18}O$, $^{33}P$, $^{34}S$ or a combination thereof. $^2H$, $^{13}C$, $^{15}N$, or $^{18}O$ or a combination thereof is preferable; $^{13}C$, $^{15}N$, or $^{18}O$ or a combination thereof is more preferable; and $^{13}C$ is especially preferable. According to the present invention, any type of isotope which can label a protein is usable with no specific limitation. Practically, $^{13}C$-labeled ($^{13}C \times 6$) leucine (produced by Cambridge Isotope Labs (CIL), L-Leucine U-$^{13}C6$, CLM-2262) is usable as a precursor of an isotope-labeled protein.

An internal standard substance of the present invention may also be prepared in vitro. For example, the proteins may be isotope-labeled by alkylating cysteine residue in the proteins using an isotope-labeled alkylating reagent (see Rapid Communications in Mass Spectroscopy, Vol. 16, No. 15 (2002), pp. 1416-1424). Alternatively, the proteins may be isotope-labeled by biotinylating cysteine residue in the proteins using an isotope-labeled biotinylating reagent. Using an adipin column, only the labeled proteins may be purified (Nature Biotechnology, Vol. 17, No. 10, October 1999, pp. 994-999).

In addition, C-terminus or N-terminus of peptide fragment, glutamic acid residue, asparaginic acid residue or the like obtained by digesting proteins may be labeled with isotope-labeled molecules. Practically, when digesting proteins with an enzyme, water labeled with $^{18}O$ is added to a buffer solution. An enzyme used for enzymatic digestion is, for example, chymotrypsin, trypsin, Asp-N, Lys-C, or Glu-C. It is known that when chymotrypsin or Asp-N is used, there is one $^{18}O$ at the C-terminus of the post-hydrolysis peptide, and that when trypsin, Lys-C, or Glu-C is used, both of two oxygen atoms of the carboxylic acid at the C-terminus of the post-hydrolysis peptide become $^{18}O$.

Furthermore, a method of methylesterifying the carboxylic acid at the C-terminus of the peptide fragment, glutamic acid residue, or asparaginic acid residue obtained by digesting proteins is known (see Goodlett D R, Keller A, Watts J D, Newitt R, Yi E C, Purvine S, Eng J K, von Haller P, Aebersold, Koller E. Differential stable isotope labeling of peptides for quantitation and de nove sequence derivation. Rapid Commun mass Spectrom. 2001:15, pp. 1214-1221). Isotope labeling may be possible by methylation using isotope-labeled methanol.

A method of forming the N-terminus of the peptide fragment obtained by digesting proteins to a nicotinic acid derivative is known (see Munchbach M, Quadroni M, Miotto G, James P. Quantitation and facilitated de novo sequencing of proteins by isotropic N-terminal labeling of peptides with a fragmentation-directing moiety. Anal. Chem. 2000:72, pp. 4047-4057), and a method of acetylation of N-terminus of the peptide (see Ji. J. Chakraborty A, Geng M, Zhang X, Amini A, Bina M, Regnier F. Strategy for quantitative and quantitative analysis in proteomics based on signature peptides. J Chromatogr B Biomed Sci Appl. 2000:745, pp. 197-210) are known. Thus, isotope labeling is also possible using such isotope-labeled reagents.

(3)(c) Step of Analyzing the Mixture Obtained in Step (b) with Mass Spectrometry This step may be performed by a method substantially the same as "1.(4)(d) Step of analyzing the mixture obtained in step (c) with mass spectrometry".

(4)(d) Step of Using a Compound-Immobilized Carrier to Purify Plural Kinds of Proteins Bound to the Compound on the Carrier, from a Group of Proteins Brought into Contact with a Compound Beforehand This step may be performed by a method substantially the same as "1.(2)(b) Step of using a compound-immobilized carrier to purify plural kinds of proteins bound to the compound on the carrier, from a group of proteins brought into contact with a compound beforehand".

The proteins used in step (d) may be a group of non-isotope-labeled proteins as in step (a). Instead of the group of non-isotope-labeled proteins, a group of isotope-labeled proteins labeled with an isotope different from the isotope used for the internal standard substance of the present invention is also usable.

(5)(e) Step of Mixing the Proteins Obtained in Step (d) and a Group of Isotope-Labeled Proteins as an Internal Standard Substance The proteins obtained in step (d) and a group of isotope-labeled proteins as an internal standard substance are mixed at a certain ratio. The certain ratio may or may not be 1:1. Here, the group of isotope-labeled proteins act as an internal standard substance. Therefore, the group of isotope-labeled proteins are preferably derived from a biological sample having the same quality as that of the plurality of proteins obtained in step (d), but may be derived from a different biological sample. Since the group of isotope-labeled proteins act as an internal standard substance, the internal standard substance of the present invention which is the same as in "3.(2)(b) Step of mixing the proteins obtained in step (a) and a group of isotope-labeled proteins as an internal standard substance" is used.

(6)(f) Step of Analyzing the Mixture Obtained in Step (e) with Mass Spectrometry This step may be performed by a method substantially the same as "1.(4)(d) Step of analyzing the mixture obtained in step (c) with mass spectrometry".

(7)(g) Step of Identifying Each of Plural Kinds of Proteins Based on Information Obtained by the Mass Spectrometry in Steps (c) and (f)

This step may be performed by a method substantially the same as "1.(5)(e) Step of identifying each of plural kinds of proteins based on information obtained by the mass spectrometry".

(8)(h) Step of Obtaining, Regarding Each Protein, an Intensity Ratio Between a Peak Derived from the Protein Obtained in Step (a) and a Peak Derived from the Protein as an Internal Standard Substance, and an Intensity Ratio Between a Peak Derived from the Protein Obtained in Step (d) and a Peak Derived from the Protein as an Internal Standard Substance, and Comparing the Two Intensity Ratios, Thereby Quantitating an Affinity Ratio of the Compound to Each Protein Using the data obtained as a result of measurement by mass spectrometry, regarding each protein, a peak intensity ratio between the peak derived from the protein obtained in step (a) or step (d) and the labeled peak derived from the internal standard substance of the present invention is obtained. By comparing the peak intensity ratios, the affinity between each protein and the compound can be quantitated.

More practically, for example, the affinity of the compound A immobilized on the carrier and non-immobilized compound B not immobilized on the carrier with respect to each protein is analyzed as follows. The peak of each of the group of proteins not brought into contact with compound B is divided by the labeled peak of the protein as the internal standard substance of the present invention. As a result, the peak/labeled peak (=peak intensity ratio A) of the protein is obtained. Separately, the peak of each of the group of proteins brought into contact with compound B is divided by the labeled peak of the protein as the internal standard substance of the present invention. As a result, the peak/labeled peak (=peak intensity ratio B) of the protein is obtained. By comparing peak intensity ratio B and peak intensity ratio A, the affinity ratio of compound A and compound B with respect to each protein can be quantitated. The comparison may be performed by, for example, calculating the ratio of peak intensity ratio B and peak intensity ratio A. The obtained value may be used as the ratio between the affinity of compound B to each protein and the affinity of compound A to the same protein.

There may be a protein which is present in the proteins obtained in step (a) or step (d) but is not present in the internal standard substance of the present invention. In this case, the peak intensity ratio is obtained, from the measurement by mass spectrometry, using a close peak derived from the internal standard substance of the present invention. Preferably, in the case of LC/MS, a peak having a close elution time in chromatography is used. In the case of MALDI-MS, a peak having a close molecular weight is used. By comparing such peak intensity ratios, the affinity ratio can be quantitated. In this manner, the affinity ratio of the protein and the compound can be measured for all the proteins obtained in step (a) or step (d).

More practically, when the affinity between compound A immobilized on the carrier and protein X, and the affinity between compound B not immobilized on the carrier and protein X, is to be compared, the following may occur. Occasionally, protein X may not be present in the internal standard substance of the present invention, and a close peak derived from protein Y may be present. Here, the expression "close peak" refers to a peak derived from the internal standard substance of the present invention, which has a close elution time in the case of LC/MS or which has a close molecular weight in the case of MALDI-MS. In this case, the peak of protein X in the group of proteins not brought into contact with non-immobilized compound B is divided by the labeled peak of the internal standard substance of the present invention, which corresponds to protein Y. Thus, the peak of protein X/the labeled peak of protein Y (=peak intensity ratio C) is obtained. Separately, the peak of protein X in the group of proteins brought into contact with compound B is divided by the labeled peak of the internal standard substance of the present invention, which corresponds to protein Y. Thus, the peak of protein X/the labeled peak of protein Y (=peak intensity ratio D) is obtained. By comparing peak intensity ratio C and peak intensity ratio D, the ratio of the affinity between compound A and protein X, and the affinity between compound B and protein X, can be quantitated. By selecting a plurality of close proteins, the precision of the measurement can be improved.

By such a method, a structural affinity relationship between plural kinds of proteins and a compound can be analyzed at the same time, simply and efficiently.

The present invention also provides a system for analyzing a structural affinity relationship between plural kinds of proteins and a compound, comprising:

(a) means for using a compound-immobilized carrier to purify plural kinds of proteins bound to the compound on the carrier, from a group of proteins;

(b) means for mixing the proteins obtained by means (a) and a group of isotope-labeled proteins as an internal standard substance;

(c) means for analyzing the mixture obtained by means (b) with mass spectrometry;

(d) means for using a compound-immobilized carrier to purify plural kinds of proteins bound to the compound on the carrier, from a group of proteins brought into contact with a compound beforehand;

(e) means for mixing the proteins obtained by means (d) and a group of isotope-labeled proteins as an internal standard substance;

(f) means for analyzing the mixture obtained by means (e) with mass spectrometry;

(g) means for identifying each of plural kinds of proteins based on information obtained by the mass spectrometry by means (c) and (f); and (h) means for obtaining, regarding each protein, an intensity ratio between a peak derived from the protein obtained by means (a) and a peak derived from the protein as an internal standard substance, and an intensity ratio between a peak derived from the protein obtained by means (d) and a peak derived from the protein as an internal standard substance, and comparing the two intensity ratios, thereby quantitating an affinity ratio of the compound to each protein.

(a) Means for using a compound-immobilized carrier to purify plural kinds of proteins bound to the compound on the carrier, from a group of proteins, is equivalent to means used for "1.(1)(a) Step of using a compound-immobilized carrier to purify plural kinds of proteins bound to the compound on the carrier, from a group of isotope-labeled proteins". The proteins used by means (a) may be a group of non-isotope-labeled proteins or a group of isotope-labeled proteins labeled with an isotope different from the isotope used for the internal standard substance of the present invention.

(b) Means for mixing the proteins obtained by means (a) and a group of isotope-labeled proteins as an internal standard substance is the same as means used for "3.(2)(b) Step of mixing the proteins obtained in step (a) and a group of isotope-labeled proteins as an internal standard substance".

(c) Means for analyzing the mixture obtained by means (b) with mass spectrometry is equivalent to means used for "1.(4)(d) Step of analyzing the mixture obtained in step (c) with mass spectrometry".

(d) Means for using a compound-immobilized carrier to purify plural kinds of proteins bound to the compound on the carrier, from a group of proteins brought into contact with a compound beforehand, is equivalent to means used for "1.(2)(b) Step of using a compound-immobilized carrier to purify plural kinds of proteins bound to the compound on the carrier, from a group of proteins brought into contact with a compound beforehand". The proteins used by means (a) may be a group of non-isotope-labeled proteins or a group of isotope-labeled proteins labeled with an isotope different from the isotope used for the internal standard substance in the present invention.

(e) Means for mixing the proteins obtained by means (d) and a group of isotope-labeled proteins as an internal standard substance is the same as means used for "3.(5)(e) Step of mixing the proteins obtained in step (d) and a group of isotope-labeled proteins as an internal standard substance".

(f) Means for analyzing the mixture obtained by means (e) with mass spectrometry is equivalent to means used for "1.(4)(d) Step of analyzing the mixture obtained in step (c) with mass spectrometry".

(g) Means for identifying each of plural kinds of proteins based on information obtained by the mass spectrometry by means (c) and (f) is equivalent to means used for "1.(5)(e) Step of identifying each of plural kinds of proteins based on information obtained by the mass spectrometry".

(h) Means, for obtaining, regarding each protein, an intensity ratio between a peak derived from the protein obtained by means (a) and a peak derived from the protein as an internal standard substance, and an intensity ratio between a peak derived from the protein obtained by means (d) and a peak derived from the protein as an internal standard substance, and comparing the two intensity ratios, thereby quantitating an affinity ratio of the compound to each protein, is the same as means used for "3.(8)(h) Step of obtaining, regarding each protein, an intensity ratio between a peak derived from the protein obtained in step (a) and a peak derived from the protein as an internal standard substance, and an intensity ratio between a peak derived from the protein obtained in step (d) and a peak derived from the protein as an internal standard substance, and comparing the two intensity ratios, thereby quantitating an affinity ratio of the compound to each protein".

Hereinafter, a system for analyzing a structural affinity relationship between plural kinds of proteins and a compound in the third embodiment of the present invention will be described. This system is equivalent to the system in the first embodiment (FIG. 6, FIG. 7, FIG. 8 and FIG. 9), but the order of the processing and the structure of the protein purification unit 602 and the protein mixing unit 603 are partially different. The protein purification unit 602 may include a protein divider in addition to the elements described in the first embodiment.

In the third embodiment of the present invention, the isotope labeling means for the proteins is provided at a different location from in the first embodiment, and the isotope-labeled substance is not mixed in the culture liquid bottle 12a in principle. The sample from the culture device 11a is the same as the sample from the culture device 11b before being brought into contact with the compound by the compound contact device 14. Therefore, the group of proteins sampled from one of two different culture devices 11a and 11b may be introduced to the compound contact device 14. Alternatively, only one culture device 11a, 11b or 11c (FIG. 10) may be used. In this case, the group of proteins sampled therefrom may be divided into a plurality of sets (e.g., the number of the non-immobilized compounds+1), and a part thereof may be brought into contact with the compound.

FIG. 10 is a schematic view of a device used for dividing a group of proteins sampled from one culture device into a plurality of sets. The group of proteins sampled from one culture device 11c are crushed by a cell crushing device 13c. Then, the central computer 30 instructs the sample divider 31 to divide the post-crushing sample into a plurality of sets, introduce a part thereof to a compound-immobilized carrier 15a and introduce the remaining part to compound contact devices 14c-1, 14c-2 and 14c-3 (FIG. 10 shows three compound contact devices). The sample divider 31 divides the sample into a plurality of sets and introduces the divided samples into the compound-immobilized carrier 15a, and the compound contact devices 14c-1, 14c-2 and 14c-3, respectively.

Separately from the proteins separated into the separators 17a and 17b, cells are cultured under a predetermined conditions by the culture device 11a, the culture liquid bottle 12a, and the cell crushing device 13a to obtain proteins. In the culture liquid bottle 12a, amino acid for isotope-labeling the group of proteins is mixed, and thus the isotope-labeled proteins as an internal standard substance are obtained.

The central computer 30 of the control unit 601 instructs the filling device (not shown) to fill the culture device 11a with a culture liquid, a sample (cell) and other reagents necessary to obtain isotope-labeled proteins as an internal standard substance. The filling device (not shown) performs the filling operation. When the culture device 11a is filled with the culture liquid and the like, the central computer 30 instructs the culture device 11a to culture under a predetermined condition. The culture device 11a performs the culture operation. When the culture operation under the predetermined condition is completed, the central computer 30 instructs the cell crushing device 13*a* to perform the cell crushing step. The cell crushing device 13*a* performs the cell crushing operation.

In the third embodiment, the protein mixing unit 603 is a unit for mixing the proteins purified by the protein purification unit 602 and the isotope-labeled proteins as an internal standard substance.

After the purified proteins are separated and temporarily stored in S906*a* and S906*b*, the central computer 30 instructs the protein mixing unit 603 to mix the separated purified proteins and the isotope-labeled proteins as an internal standard substance, and the protein mixing unit 603 performs the mixing operation (S907).

4. Fourth Embodiment of the Present Invention

A fourth embodiment of the present invention provides a method for analyzing a structural affinity relationship between plural kinds of proteins and a compound, comprising the steps of:

(a1) using a compound-immobilized carrier to purify plural kinds of proteins bound to the compound on the carrier, from a group of proteins;

(a2) analyzing the purified proteins obtained in step (a1) with mass spectrometry;

(a3) identifying each of plural kinds of proteins based on information obtained by the mass spectrometry in step (a2);

(a4) quantitating each of the plural kinds of proteins;

(b1) using a compound-immobilized carrier to purify plural kinds of proteins bound to the compound on the carrier, from a group of proteins brought into contact with a compound beforehand;

(b2) analyzing the purified proteins obtained in step (b1) with mass spectrometry;

(b3) identifying each of plural kinds of proteins based on information obtained by the mass spectrometry in step (b2);

(b4) quantitating each of the plural kinds of proteins; and (c) obtaining, regarding each protein, a ratio between an amount of the protein obtained in step (a1) and an amount of the protein obtained in step (b1), thereby quantitating an affinity ratio of the compound to each protein.

Hereinafter, the fourth embodiment of the present invention will be described in detail.

(1)(a1) Step of Using a Compound-Immobilized Carrier to Purify Plural Kinds of Proteins Bound to the Compound on the Carrier, from a Group of Proteins In this step, plural kinds of proteins bound to the compound immobilized on the carrier can be purified by a method substantially the same as "1.(1)(a) Step of using a compound-immobilized carrier to purify plural kinds of proteins bound to the compound on the carrier, from a group of isotope-labeled proteins".

The proteins used in step (a1) may be a group of non-isotope-labeled proteins. Instead of the group of non-isotope-labeled proteins, a group of isotope-labeled proteins may be used.

(2)(a2) Step of Analyzing the Purified Proteins Obtained in Step (a1) with Mass Spectrometry This step may be performed by a method substantially the same as "1.(4)(d) Step of analyzing the mixture obtained in step (c) with mass spectrometry".

(3)(a3) Step of Identifying Each of Plural Kinds of Proteins Based on Information Obtained by the Mass Spectrometry in Step (a2)

This step may be performed by a method substantially the same as "1.(5)(e) Step of identifying each of plural kinds of proteins based on information obtained by the mass spectrometry".

(4)(a4) Step of Quantitating Each of the Plural Kinds of Proteins

In this step, the method for quantitating each protein is not specifically limited, but may be performed as follows, for example.

Regarding the proteins identified in step (a3), the number of detected peptides ($N_{obsd}$) and the number of detectable peptides ($N_{obsbl}$) are calculated.

The "number of detected peptides ($N_{obsd}$)" refers to the number of peptides actually detected in "4.(2)(a2) Step of analyzing the purified proteins obtained in step (a1) with mass spectrometry". The number of detected peptides ($N_{obsd}$) may be calculated based on the mass spectrometry data and sequence information of the identified proteins. When calculated based on the mass spectrometry data, the number of detected peptides (NobSd) matches the number of peaks detected in mass spectrometry for each protein.

The "number of detectable peptides ($N_{obsbl}$)" refers to the number of peptides which can be theoretically detected in "4.(2)(a2) Step of analyzing the purified proteins obtained in step (a1) with mass spectrometry". The number of detectable peptides ($N_{obsbl}$) may be calculated based on the sequence information of the identified proteins. Regarding each protein, the number of peptides theoretically generated by the separation, digestion or the HPLC separation in the above-described steps is calculated based on the sequence information, and thus the number of peptides detectable by mass spectrometry ($N_{obsbl}$) can be obtained. For example, when mass spectrometry is performed on the purified substance treated with digestion with trypsin, the peptide chains are cut by trypsin on the carboxyl side of lysine and arginine. Therefore, the number of peptides generated by the cutting can be predicted based on the sequence information of each protein. In some cases, the number of detectable peptides ($N_{obsbl}$) may be obtained in consideration of the measurement range of the mass spectrometer.

Next, in order to quantitate each protein using the number of detectable peptides ($N_{obsbl}$) and the number of detected peptides ($N_{obsd}$), EMPAI (exponentially modified protein abundance index) is set in accordance with expression (I).

$$EMPAI = 10^{Nobsd/Nobsbl} - 1 \qquad \text{Expression (I)}$$

EMPAI is an index in proportion to the protein content in the protein mixture.

Then, the protein content (mol %) may be calculated in accordance with expression (II).

$$\text{protein content}\,(\text{mol}\,\%) = \frac{EMPAI}{\Sigma(EMPAI)} \times 100 \qquad \text{Expression (II)}$$

In the expression, Σ(EMPAI) represents the sum of EMPAIs of all the identified proteins.

The protein content (wt. %) may be calculated in accordance with expression (III).

$$\text{protein content (wt. \%)} = \frac{EMPAI \times MW}{\sum (EMPAI \times MW)} \times 100 \quad \text{Expression (III)}$$

In the expression, MW represents the molecular weight of each identified protein. Σ(EMPAI×MW) represents the sum of the EMPAI×MW values of all the identified proteins.

The molecular weight of each protein may be calculated from the amino acid sequence. The total weight of the proteins obtained in step (a1) may be easily measured by a known method, for example, the Lowry method, the Bradford method, absorbance measurement at 280 nm or the like. Based on the total weight of the proteins obtained in step (a1) and the above-obtained protein content, each protein can be quantitated.

Thus, each protein can be quantitated by the above-described method.

The step of quantitating each protein may be performed using a computer.

(5)(b1) Step of Using a Compound-Immobilized Carrier to Purify Plural Kinds of Proteins Bound to the Compound on the Carrier, from a Group of Proteins Brought into Contact with a Compound Beforehand In this step, plural kinds of proteins bound to the compound immobilized on the carrier can be purified by a method substantially the same as "1.(2)(b) Step of using a compound-immobilized carrier to purify plural kinds of proteins bound to the compound on the carrier, from a group of proteins brought into contact with a compound beforehand". The proteins used in step (b1) may be a group of non-isotope-labeled proteins. Instead of the group of non-isotope-labeled proteins, a group of isotope-labeled proteins may be used.

(6)(b2) Step of Analyzing the Purified Proteins Obtained in Step (b1) with Mass Spectrometry This method may be performed by a method substantially the same as "1.(4)(d) Step of analyzing the mixture obtained in step (c) with mass spectrometry".

(7)(b3) Step of Identifying Each of Plural Kinds of Proteins Based on Information Obtained by the Mass Spectrometry in Step (b2)

This method may be performed by a method substantially the same as "1.(5)(e) Step of identifying each of plural kinds of proteins based on information obtained by the mass spectrometry".

(8)(b4) Step of Quantitating Each of the Plural Kinds of Proteins

This method may be performed by a method substantially the same as "4.(4)(a4) Step of quantitating each of plural kinds of proteins".

(9)(c) Step of Obtaining, Regarding Each Protein, a Ratio Between an Amount of the Protein Obtained in Step (a1) and an Amount of the Protein Obtained in Step (b1), Thereby Quantitating an Affinity Ratio of the Compound to Each Protein.

In this step, the affinity between each protein and a compound can be quantitated by obtaining, regarding each protein, a ratio between an amount of the protein obtained in step (a4) and an amount of the protein obtained in step (b4).

The method in the fourth embodiment of the present invention has a feature that it is not necessary to isotope-label each protein.

The present invention also provides a system for analyzing a structural affinity relationship between plural kinds of proteins and a compound, comprising:

(a1) means for using a compound-immobilized carrier to purify plural kinds of proteins bound to the compound on the carrier, from a group of proteins;

(a2) means for analyzing the purified proteins obtained by means (a1) with mass spectrometry;

(a3) means for identifying each of plural kinds of proteins based on information obtained by the mass spectrometry by means (a2);

(a4) means for quantitating each of the plural kinds of proteins;

(b1) means for using a compound-immobilized carrier to purify plural kinds of proteins bound to the compound on the carrier, from a group of proteins brought into contact with a compound beforehand;

(b2) means for analyzing the purified proteins obtained by means (b1) with mass spectrometry;

(b3) means for identifying each of plural kinds of proteins based on information obtained by the mass spectrometry by means (b2);

(b4) means for quantitating each of the plural kinds of proteins; and (c) means for obtaining, regarding each protein, a ratio between an amount of the protein obtained by means (a1) and an amount of the protein obtained by means (b1), thereby quantitating an affinity ratio of the compound to each protein.

(a1) Means for using a compound-immobilized carrier to purify plural kinds of proteins bound to the compound on the carrier, from a group of proteins, is equivalent to means used for "1.(1)(a) Step of using a compound-immobilized carrier to purify plural kinds of proteins bound to the compound on the carrier, from a group of isotope-labeled proteins". The proteins used by means (a1) may be a group of non-isotope-labeled proteins. Instead of the group of non-isotope-labeled proteins, a group of isotope-labeled proteins may be used.

(a2) Means for analyzing the purified proteins obtained by means (a1) with mass spectrometry is equivalent to means used for "1.(4)(d) Step of analyzing the mixture obtained in step (c) with mass spectrometry".

(a3) Means for identifying each of the plural kinds of proteins based on information obtained by the mass spectrometry by means (a2) is equivalent to means used for "1.(5)(e) Step of identifying each of plural kinds of proteins based on information obtained by the mass spectrometry".

(a4) Means for quantitating each of plural kinds of proteins is the same as means used for "4.(4)(a4) Step of quantitating each of plural kinds of proteins".

(b1) Means for using a compound-immobilized carrier to purify plural kinds of proteins bound to the compound on the carrier, from a group of proteins brought into contact with a compound beforehand, is equivalent to means used for "1.(2)(b) Step of using a compound-immobilized carrier to purify plural kinds of proteins bound to the compound on the carrier, from a group of proteins brought into contact with a compound beforehand". The proteins used by means (b1) may be a group of non-isotope-labeled proteins. Instead of the group of non-isotope-labeled proteins, a group of isotope-labeled proteins may be used.

(b2) Means for analyzing the purified proteins obtained by means (b1) with mass spectrometry is equivalent to means used for "1.(4)(d) Step of analyzing the mixture obtained in step (c) with mass spectrometry".

(b3) Means for identifying each of plural kinds of proteins based on information obtained by the mass spectrometry by means (b2) is equivalent to means used for "1.(5)(e) Step of identifying each of plural kinds of proteins based on information obtained by the mass spectrometry".

(b4) Means for quantitating each of the plural kinds of proteins is the same as means used for "4.(4)(a4) Step of quantitating each of plural kinds of proteins".

(c) Means, for obtaining, regarding each protein, a ratio between an amount of the protein obtained by means (a1) and an amount of the protein obtained by means (b1), thereby quantitating an affinity ratio of the compound to each protein, is the same as means used for "4.(9)(c) Step of obtaining, regarding each protein, a ratio between an amount of the protein obtained in step (a1) and an amount of the protein obtained in step (b1), thereby quantitating an affinity ratio of the compound to each protein".

Hereinafter, a system for analyzing a structural affinity relationship between plural kinds of proteins and a compound in the fourth embodiment of the present invention will be described. This system is equivalent to the system in the first embodiment (FIG. 6, FIG. 7, FIG. 8 and FIG. 9), but the protein mixing unit 603 is omitted and the order of the processing and the structure of the protein purification unit 602 are partially different.

In the fourth embodiment of the present invention, the isotope labeling means for the proteins is provided at a different location from in the first embodiment, and the isotope-labeled substance is not mixed in the culture liquid bottle 12a in principle. The sample from the culture device 11a is the same as the sample from the culture device 11b before being brought into contact with the compound by the compound contact device 14. Therefore, the group of proteins sampled from one of two different culture devices 11a and 11b may be introduced to the compound contact device 14. Alternatively, only one culture device 11a, 11b or 11c (FIG. 10) may be used. In this case, the group of proteins sampled therefrom may be divided into a plurality of sets (e.g., the number of the non-immobilized compounds+1), and a part thereof may be brought into contact with the compound.

FIG. 10 is a schematic view of a device used for dividing a group of proteins sampled from one culture device into a plurality of sets. The group of proteins sampled from one culture device 11c are crushed by a cell crushing device 13c. Then, the central computer 30 instructs the sample divider 31 to divide the post-crushing sample into a plurality of sets, introduce a part thereof to a compound-immobilized carrier 15a and introduce the remaining part to compound contact devices 14c-1, 14c-2 and 14c-3 (FIG. 10 shows three compound contact devices). The sample divider 31 divides the sample into a plurality of sets and introduces the divided samples into the compound-immobilized carrier 15a, and the compound contact devices 14c-1, 14c-2 and 14c-3, respectively.

In the fourth embodiment, the protein mixing unit 603 is not provided. In accordance with an instruction from the control unit 601, the mass spectrometry unit prepares a sample for mass spectrometry from each of the samples contained in the purified protein separators 17a and 17b (S908), and performs mass spectrometry (S909). The central computer 30 identifies each of the proteins from the purified protein separators 17a and 17b (S910), and quantitates each of the plural kinds of proteins based on the mass spectrometry data, amino acid sequence information obtained by protein identification and the like. Thus, the central computer 30 obtains, regarding each protein, the ratio between the protein amount from the purified protein separator 17a and the protein amount from the purified protein separator 17b, and quantitates the affinity of the compound to each protein.

EXAMPLES

Hereinafter, the present invention will be described by way of practical examples, but the present invention is not limited to these examples.

(1) Production of a Compound-Immobilized Affinity Chromatography

Formula 1:

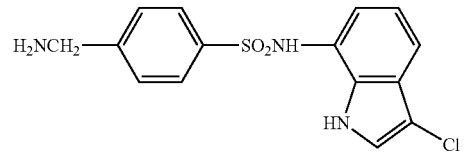

Compound (1) represented by formula 1 was produced by the method described in Japanese Laid-Open Patent Publication No. 7-165708. Next, about 52 mg of compound (1) represented by formula 1 was dissolved in 4 mL of tetrahydrofuran (THF) and 4 mL of methanol (MeOH), and 4 mL of water was added thereto.

6 mL of the resultant solution was diluted with 18 mL of THF/MeOH/Water=1/1/1 (v/v/v), and was added to 25 mL of Affi-gel 10 (produced by BioRad, Cat No. 153-6099), which had been washed with THF/MeOH/Water=1/1/1 (v/v/v) beforehand.

To the resultant substance, 100 µL of triethylamine (produced by Tokyo Chemical Industry Co., Ltd., Cat No. T0424) was added and incubated at room temperature overnight. Next morning, 100 µL of 2-aminoethanol (produced by Tokyo Chemical Industry Co., Ltd., Cat No. A0297) was added and incubated at room temperature for 3 hours. The resultant gel was fully washed with THF/MeOH/Water=1/1/1 (v/v/v), and stored at 4° C. after replacement with methanol. The resultant gel was set to be used as an affinity gel. By this reaction, compound (1) of formula 1 was bound at a ratio of about 1 mg for 1 mL of gel. A column was filled with the produced affinity gel. Thus, an affinity chromatography column was produced.

(2) Preparation of Cells

Human colon glandular cancer cell line HCT116 (ATCC) was cultured. Used as a medium was RPMI-1640 (Sigma, R-7130) containing 10% fetal calf serum (MOREGATE, BATCH 32300102), 100 U/ml of penicillin G, and 100 µg/ml of streptomycin (GIBCO, 15140-122). As for the RPMI-1640 medium, a powder medium which does not contain L-glutamine, L-lysine, L-methionine, L-leucine, or sodium hydrogen carbonate was selected. Then, components absent in the medium were added (L-glutamine (produced by Sigma, G-8540), L-lysine (produced by Sigma, L-9037), L-methionine (produced by Sigma, M-5308), and sodium hydrogen carbonate (Wako Pure Chemical Industries, Ltd., 191-01305)) were added in 0.3 g/L, 0.04 g/L, 0.015 g/L, and 2 g/L, respectively. Then, naturally-occurring L-leucine and L-leucine labeled with a stable isotope $^{13}C$ (six) (Cambridge Isotope Laboratories, CLM-2262) were separately added in 0.05 g/L. Each medium thus prepared was used to culture cells in 5% $CO_2$ at 37° C. The cells obtained by such culturing were used in the following tests as cells cultured in a naturally-occurring medium and cells cultured in a stable isotope medium, respectively.

(3) Extraction of Proteins

Cells cultured in the naturally-occurring medium were provided in an amount corresponding to 50 15-cm diameter plates. Cells cultured in the stable isotope medium were provided in an amount corresponding to 20 15-cm diameter plates. The cells were collected. The cells were solubilized with about 1.2 ml of M-PER (PIERCE, 78501) per 15-cm diameter plate. Insoluble fractions were removed by centrifugation to prepare soluble fractions. The soluble fractions thus obtained were set to be used as a protein extract liquid not metabolically labeled with a stable isotope and a protein extract liquid metabolically labeled with a stable isotope, respectively.

(4) Preparation of Compounds

Compounds (2) through (6) represented by formulas 2 through 6 were produced by the method described in Japanese Laid-Open Patent Publication No. 7-165708. Next, about 20 mg of compound (2) of formula 2, about 13 mg of compound (3) of formula 3, about 12 mg of compound (4) of formula 4, about 9 mg of compound (5) of formula 5, and about 14 mg of compound (6) of formula 6 were taken, and each compound was dissolved in DMSO so as to have a concentration of 2 mg/300 μL. It is known that these compounds have a cell proliferation inhibition activity in the strength order of compound (2)>compound (4)>compound (5)>compound (3)>compound (6) (Y. Oda, T. Owa, T. Sato, B. Boucher, S. Daniels, H. Yamanaka, Y. Shinohara, A. Yokoi, J. Kuromitsu, and T. Nagasu, Anal. Chem., 75, 2159 (2003)).

Formula 2:

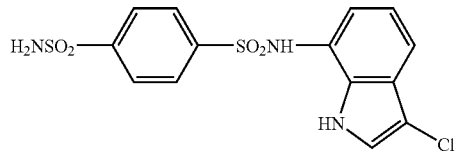

Formula 3:

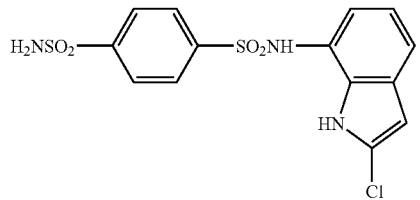

Formula 4:

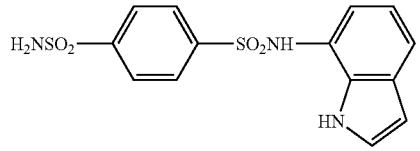

Formula 5:

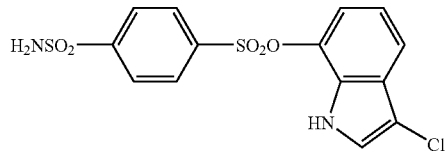

Formula 6:

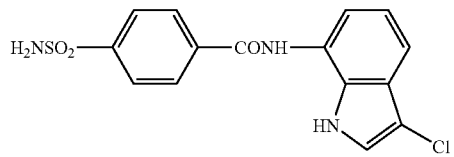

(5) Purification of a Group of Binding Proteins in a Compound-Immobilized Affinity Chromatography Column First, 20 ml of PBS was added to 10 ml of protein extract liquid metabolically labeled with a stable isotope. To the resultant substance, 300 μL of a solution of each of compounds (2) through (6) represented by formulas 2 through 6, which was prepared above (example (4)) was added and incubated at 4° C. for 3 hours. The resultant substances were each set to be used as a protein extract liquid mixed with a compound.

Next, about 1 ml of affinity gel was used as an open column, and each protein extract liquid mixed with a compound was naturally dropped thereto from above. Then, 15 ml of PBS containing 0.5 M NaCl and 0.01% CHAPS was flown to this column. Next, 6 ml of PBS containing 5 mM NaDH and 0.01% CHAPS was flown. Then, 6 ml of PBS containing 5 mM ATP and 0.01% CHAPS was flown. After this, 6 ml of liquid containing 6 M guanidine hydrochloride and 2% CHAPS was flown and eluted fractions were collected. The resultant substances were each set to be used as a purified protein solution mixed with a compound.

In parallel with the above, 40 ml of PBS was added to 20 ml of protein extract liquid not metabolically labeled with a stable isotope, and the resultant liquid was divided into two, i.e., 30 ml for each. Two open column tubes each containing about 1 ml of affinity gel were prepared, and the divided extract liquid was naturally dropped to the open column tubes from above. Then, 15 ml of PBS containing 0.5 M NaCl and 0.01% CHAPS was flown to this column. Next, 6 ml of PBS containing 5 mM NaDH and 0.01% CHAPS was flown. Then, 6 ml of PBS containing 5 mM ATP and 0.01% CHAPS was flown. After this, 6 ml of liquid containing 6 M guanidine hydrochloride and 2% CHAPS was flown, and eluted fractions were collected. The resultant substances were each set to be used as a purified protein solution not mixed with a compound.

The purified protein solution mixed with a compound, and the purified solution liquid not mixed with a compound, were mixed together at a ratio of 3:1. The mixed solution was enriched with Amicon Ultra-15 10,000 MWCO (Millipore, Cat No. UFC901096) and repeatedly washed with 50 mM ammonia hydrogen carbonate water, separated with SDS-PAGE (DRC K.K., 5 to 20% T gel, 1 mm, 7 wells, 4 cm, 200 V), and digested with trypsin in a gel in an electrophoresis lane equally divided into 12. The resultant solution was set to be used as a digested protein solution (H. Katayama, K. Satoh, M. Takeuchi, M. Deguchi-Tawarada, Y. Oda and T. Nagasu, Rapid Commun. Mass Spectrom. 17, 1071-1078 (2003)).

(6) Measurement with LC/MS

The digested protein solution was dissolved in 5% acetonitrile containing 0.1% trofluoroacetic acid, and the resultant substance was set to be used as a protein solution as a target of measurement. MS of LC/MS was performed using LCQ-Duo (produced by Thermo Electron). LC of LC/MS was performed as follows. 0.5% acetic acid as a mobile phase was incorporated into a home-produced ODS column (Y. Ishihama, J. Rappsilber, J. S. Andersen, M. Mann, J. Chromatogr A. 979, 233-239 (2002)) (inner diameter: 0.2 mm; length: about 15 cm). Over the first 1 minute, the acetonitrile concentration was reduced to 4%. Then, over the subsequent 35 minutes, the acetonitrile concentration was linearly increased to 20%. Then, within 0.1 minute, the acetonitrile concentration was increased to 80%, which was kept for 5 minutes. Then, the acetonitrile concentration was reduced to 0%. 12 minutes later, the next sample was implanted.

As the pump, an LC-10A series device of Shimadzu Corporation was used with the ROM being made compatible to the order of micrometers. As the mixing chamber, T connector of Barco was used instead of the attached chamber produced by Shimadzu.

For the flow rate, the flow-splitting system was used. The flow rate in the column was adjusted to be 1 to 2 μL per minute. The protein solution as the target of measurement was implanted in 10 μL by PAL Autosampler of CTC. Ions obtained by directly spraying the eluted substance from the column outlet were transferred to the LCQ to perform the measurement. As a spray voltage, 2.5 kV was applied. The measurement was performed in the Data Dependent mode, with the Repeat of Dynamic Exclusion of 1. In order to maximize the number of times of scanning, the so-called double play mode was used for the measurement, without the zoom scan mode.

(7) Data Analysis

The proteins were automatically identified using SonarMSMS (Genomic Solution) and the NCBInr database. The program was partially modified such that even leucine labeled with a stable isotope could be searched for in the NCBInr.

Quantitation was to be performed at the peak of the peptides containing leucine. Therefore, only the peptides containing leucine were selected from the peptides identified by SonarMSMS. In order to specify the elution position at the peptide peak (retaining time with HPLC=scanning number with MS), software for automatically selecting scanning information from the LCQ_dta.exe file, packaged in LCQ duo, was constructed. Based on the scanning number information, the MS spectrum of the scanning number was extracted. Regarding the peak of the naturally-occurring leucine peptides and the peak of the isotope peptides, information on the parent ions (m(mass)/z(charge) value) when the MS/MS was performed, how many leucines are contained in the peptides, and how many charges are present, were obtained from the search result of SonarMSMS. Peaks forming a pair were found, and the peak intensity ratio thereof was automatically calculated. In this manner, proteins were identified and the peak intensity ratio was calculated using the constructed software.

FIG. 5 shows an example of the obtained results. FIG. 5 shows the structural affinity relationship between plural kinds of proteins and compounds (2) (formula 2) through (6) (formula 6). A smaller numeral represents a stronger affinity.

From FIG. 5, the following information, for example, cam be obtained.

(1) By checking the figure in the column direction, it is understood, for example, that to compound (3) (formula 3), glutathione-S-transferase omega 1 has the strongest affinity and heme binding protein 1 has the second strongest affinity. Thus, the order of the strength of affinity is understood. It is understood which proteins, other than the target protein, compound (3) has a strong affinity to (FIG. 5).

(2) By checking the figure in the row direction, with respect to one protein, for example, with respect to glutathione-S-transferase omega 1, the information can be obtained that when compounds are to be synthesized using that protein as a target, compound (4) (formula 4) has a stronger affinity than compound (3) and compound (6) (formula 6) has a weaker affinity than compound (3) (formula 3) (FIG. 5).

With the method according to the present invention, it can be comprehensively analyzed how a structural change of a compound will influence the affinity with the protein. As a result, information useful for synthesizing compounds, especially drugs, which enhance main actions while reducing side effects is made available.

(3) If the figure contains one point at which the affinity is strong both in the column direction and the row direction, it is found that the corresponding combination of the compound and the protein has a high specificity. The protein is considered to be the target protein of the compound.

INDUSTRIAL APPLICABILITY

According to the present invention, a structural affinity relationship between plural kinds of proteins and a compound can be analyzed at the same time, simply and efficiently.

According to the present invention, it is not necessary any more to prepare a plurality of affinity chromatography columns having a compound immobilized thereon. Information on the structural affinity relationship based on a plurality of compounds can be obtained simply and efficiently. Only one of the compounds is immobilized and the other compounds are used without being immobilized. Therefore, the affinity of each compound to the protein can be evaluated while the original structure of each compound is maintained. Thus, more accurate information on the structural affinity relationship is made available.

According to the present invention, it is made possible to conduct a comprehensive analysis on the affinity with which protein is influenced by a structural change of a compound. As a result, information useful for synthesizing and developing compounds, especially drugs, which enhance main actions while reducing side effects is made available. For example, according to the present invention, information on the structural affinity relationship is made available using a carrier having NAD or NADP immobilized thereon. As a result, it is made possible to conduct a comprehensive analysis on the affinity of what type of dehydrogenase is influenced by a structural change of a compound. This provides information on specificity, selectivity or the like which is useful for screening dehydrogenase inhibitors. For example, according to the present invention, information on the structural affinity relationship is made available using a carrier having ATP or GTP immobilized thereon. Thus, it is made possible to conduct a comprehensive analysis on the affinity with what type of kinase, ATP-ase or GTP-ase is influenced by a structural change of a compound. This provides information on specificity, selectivity or the like which is useful for screening the inhibitors against these substances.

A compound immobilized on the carrier (e.g., an affinity chromatography column) generally has a concentration of about 0.1 mg to several milligrams with respect to 1 ml of gel, which corresponds to about 1 mM. However, it is known that a compound having some activity on a cell exhibits the activity by the order of several micromoles to several nanomoles, or sometimes by the order of several picomoles. This is significantly different from a concentration of the compound immobilized on the carrier (e.g., an affinity chromatography column). According to the present invention, compounds are used without being immobilized on the carrier. This makes it possible to reduce the concentration of the compound from several micromoles to several nanomoles to realize a state closer to a compound in a biological body.

The invention claimed is:

1. A method for analyzing a structural affinity relationship between plural kinds of proteins and plural kinds of test compounds, comprising the steps of:
(a) using a detection compound-immobilized carrier to purify plural kinds of 1st isotope-labeled proteins bound to the detection compound immobilized on the detection compound-immobilized carrier, from a 1st group of proteins labeled with the 1st isotope;

(b) using the detection compound-immobilized carrier to purify plural kinds of proteins, which may or may not be labeled with a 2nd isotope, bound to the detection compound immobilized on the detection compound-immobilized carrier, from a 2nd group of proteins, which may or may not be labeled with the 2nd isotope, wherein the 2nd group of proteins is brought into contact with a 1st test compound before using the detection compound-immobilized carrier;

(c) using the detection compound-immobilized carrier to purify plural kinds of proteins, which may or may not be labeled with the 2nd isotope, bound to the detection compound immobilized on the detection compound-immobilized carrier, from a 3rd group of proteins, which may or may not be labeled with the 2nd isotope, wherein the 3rd group of proteins is brought into contact with a 2nd test compound before using the detection compound-immobilized carrier;

wherein the detection compound is the same for steps (a) to (c), wherein the 1st test compound is the same compound as the detection compound, wherein the 1st and 2nd isotopes are different from each other, wherein the 1st and 2nd test compounds are different from each other, wherein the 1st group of proteins does not have contact with the 1st or 2nd test compound, wherein the 2nd group of proteins does not have contact with the 2nd test compound, and wherein the 3rd group of proteins does not have contact with the 1st test compound before using the detection-compound-immobilized carrier;

(d) mixing the plural kinds of proteins purified in step (a) together with the plural kinds of proteins purified in step (b) to prepare a 1st protein mixture;

(e) analyzing the plural kinds of proteins in the 1st protein mixture prepared in step (d) with mass spectrometry;

(f) identifying each of the plural kinds of proteins analyzed in step (e) based on information obtained by the mass spectrometry performed in step (e);

(g) mixing the plural kinds of proteins purified in step (a) together with the plural kinds of proteins purified in step (c) to prepare a 2nd protein mixture;

(h) analyzing the plural kinds of proteins in the 2nd protein mixture prepared in step (g) with mass spectrometry;

(i) identifying each of the plural kinds of proteins analyzed in step (h) based on information obtained by the mass spectrometry performed in step (h); and (j) obtaining, regarding each identified protein, an intensity ratio between a peak derived from one of the plural kinds of proteins purified in step (a) and a peak derived from one of the plural kinds of proteins purified in step (b) and an intensity ratio between a peak derived from one of the plural kinds of proteins purified in step (a) and a peak derived from one of the plural kinds of proteins purified in step (c), thereby quantitating affinity ratios of the 1st and 2nd test compounds to each identified protein.

2. A method for analyzing a structural affinity relationship between plural kinds of proteins and plural kinds of test compounds, comprising the steps of:

(a) using a detection compound-immobilized carrier to purify plural kinds of proteins, which may or may not be labeled with a 1st isotope, bound to the detection compound immobilized on the detection compound-immobilized carrier, from a 1st group of proteins, which may or may not be labeled with the 1st isotope;

(b) using the detection compound-immobilized carrier to purify plural kinds of 2nd isotope-labeled proteins bound to the detection compound immobilized on the detection compound-immobilized carrier, from a 2nd group of proteins labeled with the 2nd isotope, wherein the 2nd group of proteins is brought into contact with a 1st test compound before using the detection compound-immobilized carrier;

c) using the detection compound-immobilized carrier to purify plural kinds of proteins with a 2nd isotope-labeled proteins bound to the detection compound immobilized on the detection compound-immobilized carrier, from a 3rd group of proteins labeled with the 2nd isotope, wherein the 3rd protein group is brought into contact with a 2nd test compound before using the detection compound-immobilized carrier;

wherein the detection compound is the same for steps (a) to (c), wherein the 1st test compound is the same compound as the detection compound, wherein the 1st and 2nd isotopes are different from each other, wherein the 1st and 2nd test compounds are different from each other, wherein the 1st group of proteins does not have contact with the 1st or 2nd test compound, wherein the 2nd group of proteins does not have contact with the 2nd test compound, and wherein the 3rd group of proteins does not have contact with the 1st test compound before using the detection-compound-immobilized carrier;

(d) mixing the plural kinds of proteins purified in step (a) together with the plural kinds of proteins purified in step (b) to prepare a 1st protein mixture;

(e) analyzing the plural kinds of proteins in the 1st protein mixture prepared in step (d) with mass spectrometry;

(f) identifying each of the plural kinds of proteins analyzed in step (e) based on information obtained by the mass spectrometry performed in step (e);

(g) mixing the plural kinds of proteins purified in step (a) together with the plural kinds of proteins purified in step (c) to prepare a 2nd protein mixture;

(h) analyzing the plural kinds of proteins in the 2nd protein mixture prepared in step (g) with mass spectrometry;

(i) identifying each of the plural kinds of proteins analyzed in step (h) based on information obtained by the mass spectrometry performed in step (h); and (j) obtaining, regarding each identified protein, an intensity ratio between a peak derived from one of the plural kinds of proteins purified in step (a) and a peak derived from one of the plural kinds of proteins purified in step (b) and an intensity ratio between a peak derived from one of the plural kinds of proteins purified in step (a) and a peak derived from one of the plural kinds of proteins purified in step (c), thereby quantitating affinity ratios of the 1st and 2nd test compounds to each identified protein.

3. A method for analyzing a structural affinity relationship between plural kinds of proteins and plural kinds of test compounds, comprising the steps of:

(a) using a detection compound-immobilized carrier to purify plural kinds of proteins bound to the detection compound immobilized on the detection compound-immobilized carrier, from a 1st group of proteins;

(b) using the detection compound-immobilized carrier to purify plural kinds of proteins bound to the detection compound immobilized on the detection compound-immobilized carrier, from a 2nd group of proteins, wherein the 2nd group of proteins is brought into contact with a 1st test compound before using the detection compound-immobilized carrier;

(c) using the detection compound-immobilized carrier to purify plural kinds of proteins bound to the detection compound immobilized on the detection compound-immobilized carrier, from a 3rd group of proteins, wherein the 3rd group of proteins is brought into contact with a 2nd test compound before using the detection compound-immobilized carrier;

(d) labeling the plural kinds of proteins purified in step (a) with a 1st isotope and optionally labeling the plural kinds of proteins purified in steps (b) and (c) with a 2nd isotope, wherein the optional labeling of the plural kinds of proteins purified in steps (b) and (c) with the 2nd isotope may or may not be performed;

(e) mixing the plural kinds of proteins purified in step (a) that are labeled with the 1st isotope in step (d) with the plural kinds of proteins purified in step (b) that are labeled with the 2nd isotope or non-labeled in step (d) to prepare a 1st protein mixture;

(f) analyzing the plural kinds of proteins in the 1st protein mixture prepared in step (e) with mass spectrometry;

(g) identifying each of the plural kinds of proteins analyzed in step (f) based on information obtained by the mass spectrometry performed in step (f);

(h) mixing the plural kinds of proteins purified in step (a) that are labeled with the 1st isotope in step (d) with the plural kinds of proteins purified in step (c) that are labeled with the 2nd isotope or non-labeled in step (d) to prepare a 2nd protein mixture;

(i) analyzing the plural kinds of proteins in the 2nd protein mixture prepared in step (h) with mass spectrometry;

(j) identifying each of the plural kinds of proteins analyzed in step (i) based on information obtained by the mass spectrometry performed in step (i); and (k) obtaining, regarding each identified protein, an intensity ratio between a peak derived from one of the plural kinds of proteins purified in step (a) and a peak derived from one of the plural kinds of proteins purified in step (b) and an intensity ratio between a peak derived from one of the plural kinds of proteins purified in step (a) and a peak derived from one of the plural kinds of proteins purified in step (c), thereby quantitating affinity ratios of the 1st and 2nd compounds to each identified protein, wherein the detection compound is the same for steps (a) to (c), wherein the 1st test compound is the same compound as the detection compound, wherein the 1st and 2nd isotopes are different from each other, wherein the 1st and 2nd test compounds are different from each other, wherein the 1st group of proteins does not have contact with the 1st or 2nd test compound, wherein the 2nd group of proteins does not have contact with the 2nd test compound, and wherein the 3rd group of proteins does not have contact with the 1st test compound before using the detection-compound-immobilized carrier.

4. A method for analyzing a structural affinity relationship between plural kinds of proteins and plural kinds of test compounds, comprising the steps of:

(a) using a detection compound-immobilized carrier to purify plural kinds of proteins, which may or may not be labeled with a 1st isotope, bound to the detection compound immobilized on the detection compound-immobilized carrier, from a 1st group of proteins;

(b) mixing the plural kinds of proteins purified in step (a) together with a 2nd group of 2nd isotope-labeled proteins as an internal standard substance to prepare a 1st protein mixture;

(c) analyzing the plural kinds of proteins in the 1st protein mixture prepared in step (b) with mass spectrometry;

(d) using the detection compound-immobilized carrier to purify plural kinds of proteins, which may or may not be labeled with the 1st isotope, bound to the detection compound immobilized on the detection compound-immobilized carrier, from a 3rd group of proteins brought into contact with a 1st test compound before using the detection compound-immobilized carrier;

(e) mixing the plural kinds of proteins purified in step (d) together with the 2nd group of 2nd isotope-labeled proteins as an internal standard substance to prepare a 2nd protein mixture;

(f) analyzing the plural kinds of proteins in the 2nd protein mixture prepared in step (e) with mass spectrometry;

(g) using the detection compound-immobilized carrier to purify plural kinds of proteins, which may or may not be labeled with the 1st-isotope, bound to the detection compound immobilized on the detection compound-immobilized carrier, from a 4th group of proteins brought into contact with a 2nd test compound before using the detection compound-immobilized carrier;

(h) mixing the plural kinds of proteins purified in step (g) together with the 2nd group of 2nd isotope-labeled proteins as an internal standard substance to prepare a 3rd protein mixture;

(i) analyzing the plural kinds of proteins in the 3rd protein mixture prepared in step (h) with mass spectrometry;

(j) identifying each of the plural kinds of proteins analyzed in steps (c), (f) and (i) based on information obtained by the mass spectrometry in steps (c), (f) and (i); and (k) obtaining, regarding each identified protein, an intensity ratio between a peak derived from one of the plural kinds of proteins obtained in step (a) and a peak derived from one of the 2nd isotope-labeled proteins as an internal standard substance, an intensity ratio between a peak derived from one of the plural kinds of proteins obtained in step (d) and a peak derived from one of the 2nd isotope-labeled proteins as an internal standard substance, and an intensity ratio between a peak derived from one of the plural kinds of proteins obtained in step (g) and a peak derived from one of the 2nd isotope-labeled proteins as an internal standard substance and comparing each intensity ratio, thereby quantitating affinity ratios of the 1st and 2nd test compounds to each identified protein, wherein the detection compound is the same for steps (a), (d) and (g), wherein the 1st test compound is the same compound as the detection compound, wherein the 1st and 2nd isotopes are different from each other, wherein the 1st and 2nd test compounds are different from each other, wherein the 1st group of proteins does not have contact with the 1st or 2nd test compound, wherein the 3rd group of proteins does not have contact with the 2nd test compound, and wherein the 4th group of proteins does not have contact with the 1st test compound before using the detection-compound-immobilized carrier.

5. A method for analyzing a structural affinity relationship between plural kinds of proteins and plural kinds of test compounds, comprising the steps of:
(a1) using a detection compound-immobilized carrier to purify plural kinds of proteins bound to the detection compound immobilized on the detection compound-immobilized carrier, from a 1st group of proteins;
(a2) analyzing the plural kinds of proteins purified in step (a1) with mass spectrometry;
(a3) identifying each of the plural kinds of proteins analyzed in step (a2) based on information obtained by the mass spectrometry in step (a2);
(a4) quantitating amounts of each of the plural kinds of proteins identified in step (a3) by mass spectrometry;
(b1) using the detection compound-immobilized carrier to purify plural kinds of proteins bound to the detection compound immobilized on the detection compound-immobilized carrier, from a 2nd group of proteins brought into contact with a 1st test compound before using the detection compound-immobilized carrier;
(b2) analyzing the plural kinds of proteins purified in step (b1) with mass spectrometry;
(b3) identifying each of the plural kinds of proteins analyzed in step (b2) based on information obtained by the mass spectrometry in step (b2);
(b4) quantitating amounts of each of the plural kinds of proteins identified in step (b3) by mass spectrometry;
(c1) using the detection compound-immobilized carrier to purify plural kinds of proteins bound to the compound immobilized on the carrier, from a 3rd group of proteins brought into contact with a 2nd test compound before using the detection compound-immobilized carrier;
(c2) analyzing the plural kinds of proteins purified in step (c1) with mass spectrometry;
(c3) identifying each of the plural kinds of proteins analyzed in step (c2) based on information obtained by the mass spectrometry in step (c2);
(c4) quantitating amounts of each of the plural kinds of proteins identified in step (c3) by mass spectrometry; and
(d) obtaining, regarding each identified protein, a ratio between an amount of one of the plural kinds of proteins obtained in step (a1) and an amount of one of the plural kinds of proteins obtained in step (b1) and a ratio between an amount of one of the plural kinds of proteins obtained in step (a1) and an amount of one of the plural kinds of proteins obtained in step (c1), thereby quantitating affinity ratios of the 1st and 2nd compounds to each identified protein,
wherein the detection compound is the same for steps (a1), (b1) and (c1),
wherein the 1st test compound is the same compound as the detection compound,
wherein the 1st and 2nd test compounds are different from each other,
wherein the 1st group of proteins does not have contact with the 1st or 2nd test compound,
wherein the 2nd group of proteins does not have contact with the 2nd test compound, and
wherein the 3rd group of proteins does not have contact with the 1st test compound before using the detection-compound-immobilized carrier.

6. The method according to any one of claims 1 through 5, wherein the detection compound-immobilized carrier is a carrier for affinity chromatography.

7. The method according to any one of claims 1 through 3, wherein the 2nd and 3rd groups of proteins are brought into contact with plural kinds of test compounds before using the detection compound-immobilized carrier.

8. The method according to claim 4, wherein the 3rd and 4th groups of proteins are brought into contact with plural kinds of test compounds before using the detection compound-immobilized carrier.

9. The method according to claim 5, wherein the 2nd and 3rd groups of proteins are brought into contact with plural kinds of test compounds before using the detection compound-immobilized carrier.

10. The method according to any one of claims 1 through 5, wherein the detection compound is a compound selected from the group consisting of ATP, GTP, NAD and NADP.

11. The method according to any one of claims 1 through 4, wherein the 1st isotope is an isotope selected from the group consisting of $^{2}H$, $^{13}C$, $^{15}N$, $^{17}O$, $^{18}O$, $^{33}P$ and $^{34}S$, and the 2nd isotope is an isotope selected from the group consisting of $^{2}H$, $^{13}C$, $^{15}N$, $^{17}O$, $^{18}O$, $^{33}P$ and $^{34}S$, wherein the 1st and 2nd isotopes are different from each other.

12. The method according to claim 11, wherein the 1st isotope is $^{13}C$.

13. The method according to claim 11, wherein the 2nd isotope is $^{13}C$.

* * * * *